United States Patent
Yue et al.

(10) Patent No.: US 11,484,536 B2
(45) Date of Patent: Nov. 1, 2022

(54) METHOD OF TREATING METASTATIC CANCER IN A SUBJECT WITH A PROTEIN INHIBITOR

(71) Applicants: City University of Hong Kong, Kowloon (HK); 6J Biotechnology (Hong Kong) Limited, New Territories (HK)

(72) Inventors: Jianbo Yue, Kowloon (HK); Qingru Zhang, New Territories (HK); Zuodong Ye, Kowloon (HK); Dawei Wang, Kowloon (HK); Kaiyuan Zhu, New Territories (HK)

(73) Assignees: City University of Hong Kong, Kowloon (HK); 6J Biotechnology Limited, New Territories (HK)

( * ) Notice: Subject to any disclaimer, the term of this patent is extended or adjusted under 35 U.S.C. 154(b) by 0 days.

(21) Appl. No.: 16/937,995

(22) Filed: Jul. 24, 2020

(65) Prior Publication Data

US 2022/0023307 A1  Jan. 27, 2022

(51) Int. Cl.
| | | |
|---|---|---|
| *A61K 31/5377* | (2006.01) | |
| *A61P 35/04* | (2006.01) | |
| *A61K 31/436* | (2006.01) | |
| *A61K 31/337* | (2006.01) | |
| *A61K 31/513* | (2006.01) | |
| *A61K 31/704* | (2006.01) | |

(52) U.S. Cl.
CPC ........ *A61K 31/5377* (2013.01); *A61K 31/337* (2013.01); *A61K 31/436* (2013.01); *A61K 31/513* (2013.01); *A61K 31/704* (2013.01); *A61P 35/04* (2018.01)

(58) Field of Classification Search
CPC .............. A61K 31/5377; A61K 31/337; A61K 31/436; A61K 31/513; A61K 31/704; A61P 35/04
USPC ......................................................... 514/34
See application file for complete search history.

(56) References Cited

U.S. PATENT DOCUMENTS 10,894,051 B2 *  1/2021  Yue ...................... A61K 9/0019
2018/0344744 A1 * 12/2018  Yue ...................... A61K 9/0053

FOREIGN PATENT DOCUMENTS

WO    WO 03/050237    *  6/2003

OTHER PUBLICATIONS

Huang et al. CAPZA1 modulates EMT by regulating actin cytoskeleton remodelling in hepatocellular carcinoma. Journal of Experimental & Clinical Cancer Research (2017) 36:13 (9 pages) (Year: 2017).*
Ye et al. Vacuolin-1 inhibits endosomal trafficking and metastasis via CapZβ. Oncogene (2021) 40:1775-1791. (Year: 2021).*
Chen et al. Identification of Novel Vacuolin-1 Analogues as Autophagy Inhibitors by Virtual Drug Screening and Chemical Synthesis. Molecules 2017, 22, 891 (13 pages) (Year: 2017).*

* cited by examiner

*Primary Examiner* — Yih-Horng Shiao
(74) *Attorney, Agent, or Firm* — Renner Kenner Greive Bobak Taylor & Weber

(57) ABSTRACT

A method of treating metastatic cancer in a subject in need thereof including administering an effective amount of a capping protein Z inhibitor to the subject. A method of inhibiting metastasis of cancer cells including administering an effective amount of a capping protein Z inhibitor.

11 Claims, 52 Drawing Sheets
(6 of 52 Drawing Sheet(s) Filed in Color)

METHOD OF TREATING METASTATIC CANCER IN A SUBJECT WITH A PROTEIN INHIBITOR

TECHNICAL FIELD

The present application relates to a method of treating metastatic cancer in a subject, in particular but not exclusively includes administering a small chemical compound such as a protein inhibitor to the subject in particular a mammal. The present application also relates to a method of inhibiting metastasis of cancer cells.

BACKGROUND OF THE INVENTION

Metastasis of cancer refers to a spread of cancer cells from one part of the body to nearby tissues, organs or even distant parts of the body. Some cancer cells may have the ability to penetrate the blood vessels and lymphatic vessels and therefore travel around the body via the blood circulation and lymphatic system. Once the cancer cells metastasize, new tumors are usually found on a second site of the body and this is called metastatic cancer. For example, but not limiting, common sites where cancer spreads are bone, liver, and lung.

Once cancer cells metastasize, it can be hard to control. Metastasis remains as the major cause of mortality accounting for about 90% of total cancer deaths. Although there are methods to treat some types of metastatic cancer, most of the currently available methods are found to be not as effective as desired. In particular, there is currently no drug on the market that can effectively treat or inhibit metastasis of cancers.

As treatment options for metastatic cancer are limited, there remains a strong need for novel compounds which are effective against metastasis of cancer and in the treatment of metastatic cancer.

SUMMARY OF THE INVENTION

It is found that various approaches may be applied to target different stages of metastasis, e.g., inhibiting the epithelial-mesenchymal transition (EMT) or the mesenchymal-epithelial transition (MET), or suppressing the motility, invasion, and/or adhesion of cancer cells. However, most of them are failed in the clinical setting either due to drug resistance or serious side effects. Likewise, compounds targeting actoinyosin contractility and actin polymerization, e.g., latrunculin A, chondramide, TR100, RIG-18, BDP5290 and DJ14, and CCT129254, are all possess high cytotoxicity to mammalian cells.

Without being bound by theory, the inventors found that small chemical compounds, 6-morpholino-1,3,5-triazine derivatives are useful in treating metastatic cancer. They found that capping protein Z (CapZ) is transiently recruited to RAB-5-loaded early endosomes, and this facilitates the enrichment of RAB5 effectors, e.g. RABEX5 and RABEP1, on the endosomes to induce early endosome maturation; and subsequently, CapZ is released from the matured earlier endosomes such that the early endosomes are transitioned to late endosomes. Meanwhile, the 6-morpholino-1,3,5-triazine derivatives are found to target CapZ, inhibiting its release from the early endosome, which consequently induces a cascade of cellular trafficking disruption and cell migration interruption.

In contrast to the metastatic drugs as described above, the 6-morpholino-1,3,5-triazine derivatives are effective in suppressing the metastasis of cancer cells while possessing low toxicity both in vitro and in vivo, as demonstrated in the examples of the later part of this disclosure. Accordingly, it is believed that these compounds are effective in treating metastatic cancer, and may be further applied in the development of medicament for treating metastatic cancer.

In the first aspect, the present invention provides a method of treating metastatic cancer in a subject in need thereof comprising administering an effective amount of a capping protein Z (CapZ) inhibitor to the subject. In a preferred embodiment, the metastatic cancer is a breast cancer.

In an embodiment, the CapZ inhibitor administered according to the present invention comprises a structure of Formula (I):

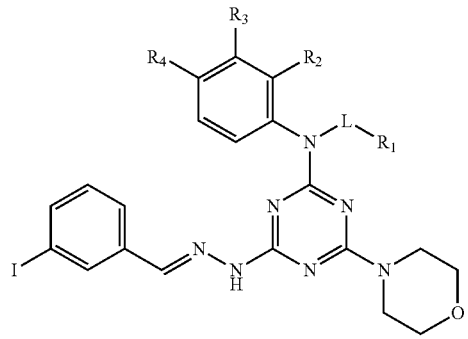

Formula (I)

wherein:

$R_1$, $R_2$, $R_3$ and $R_4$ are independently selected from a hydrogen atom, a saturated or unsaturated C1-C5 alkyl group, a cyano group, a C2-C5 alkoxycarbonyl group, a C5-C8 carbocyclic ring, a C1-C5 alkoxy group, or a halogen atom;

L is a linker group of —$(CH_2)_m$— or —$(CH_2CH_2O)_{m'}$— with m and m' being 0 or any positive integer.

In particular embodiment, the CapZ inhibitor has a structure of Formula (I) with $R_1$ being selected from a hydrogen atom, a saturated or unsaturated C1-C3 alkyl group, a cyano group, a C2-C5 alkoxycarbonyl group, a C5-C8 carbocyclic ring; $R_2$, $R_3$ and $R_4$ being independently selected from a hydrogen atom, a saturated or unsaturated C1-C3 alkyl group, a C1-C5 alkoxy group, or a halogen atom, wherein each adjacent pair of $R_2$, $R_3$ and $R_4$ may form a fused heterocyclic or carbocyclic ring; and L being a linker group of —$(CH_2)_m$— or —$(CH_2CH_2O)_{m'}$— with m and m' being 0, 1, 2, 3, 4, or 5.

In a preferred embodiment, the CapZ inhibitor has a structure of Formula (I) with $R_1$ being a hydrogen atom, a methyl group, a cyano group, an ethynyl group, an ethoxycarbonyl group, or a phenyl group; $R_2$ and $R_3$ being independently a hydrogen atom, a methoxy group, or an ethoxycarbonyl group; $R_4$ being a hydrogen atom, a chloro or a fluoro group; and L being a linker group of —$(CH_2)_m$— or —$(CH_2CH_2O)_{m'}$— with m being 0, 3, 4 or 5, and m' being 0 or 2.

In another embodiment, the CapZ inhibitor has a structure of Formula (I) with $R_1$ being a hydrogen atom, a methyl group, a cyano group, an ethynyl group, an ethoxycarbonyl group, or a phenyl group; $R_2$ and $R_3$ together forming a fused 6-membered aromatic carbocyclic ring; $R_4$ being a hydrogen atom, a chloro or a fluoro group; and L being a linker group of —$(CH_2)_m$— or —$(CH_2CH_2O)_{m'}$— with m being 0, 3, 4 or 5, and m' being 0 or 2.

In an embodiment, the CapZ inhibitor has a structure of Formula (II):

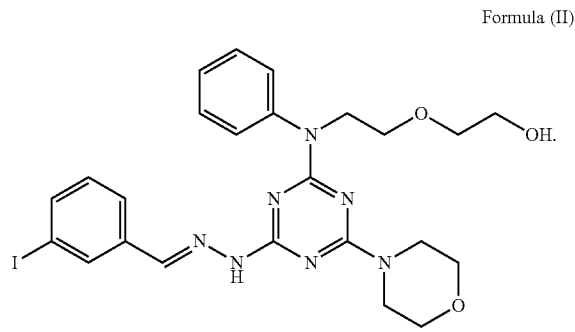

Formula (II).

In an embodiment, the CapZ inhibitor is administered to the subject by a route selected from the group consisting of oral delivery, intravenous delivery, intradermal delivery, intraperitoneal delivery and intramuscular delivery.

In an embodiment, the CapZ inhibitor is administered in combination with one or more chemotherapy drug to the subject. In particular, the chemotherapy drug is selected from doxorubicin, taxol, 5-Fu, or temirolimus.

In the second aspect, the present invention pertains to a method of inhibiting metastasis of cancer cells comprising administering an effective amount of a CapZ inhibitor as described above. In an embodiment, the cancer cells are breast cancer cells.

In an embodiment, the CapZ inhibitor is contacted with the cells in combination with one or more chemotherapy drug, particularly selected from doxorubicin, taxol, 5-Fu, or temirolimus.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1A:
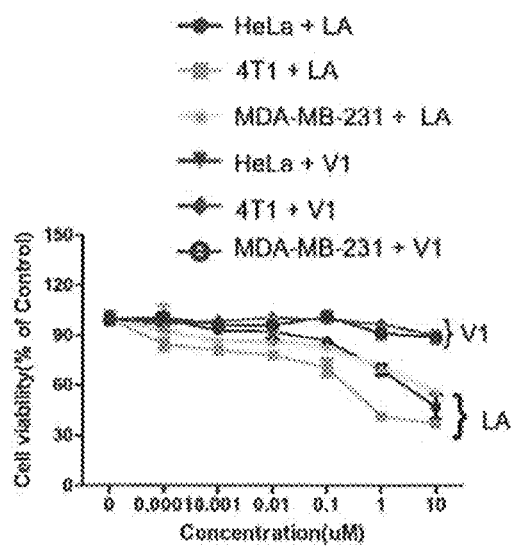
FIG. 1A is a series of line charts showing the cell viability of 4T1, MDA-MB-231, and HeLa cells treated with or without V1 or LA at indicated concentrations for 24 or 48 h.

Unless otherwise defined, all technical terms used herein have the same meaning as commonly understood by one skilled in the art to which the invention belongs.

As used herein, "comprising" means including the following elements but not excluding others. "Consisting of"

means that the material solely consists of, i.e. is formed by the respective element. As used herein, the forms "a," "an," and "the", are intended to include the singular and plural forms unless the context clearly indicates otherwise.

The present invention in the first aspect provides a method of treating metastatic cancer in a subject in need thereof. The method comprises administering an effective amount of a capping protein Z (CapZ) inhibitor to the subject.

The metastatic cancer as used herein refers to cancer cells having the ability to spread from one site in the body of a subject to a second site in the body of a subject, in particular to a non-adjacent part of the body. The cancer may be selected from the group consisting of bladder cancer, breast cancer, colon cancer, kidney cancer, lung cancer, ovary cancer, skin cancer, pancreatic cancer, prostate cancer, liver cancer and bone cancer.

In particular, the cancer is a breast cancer, a liver cancer or a lung cancer. Preferably, the cancer is a breast cancer.

"Treating" the metastatic cancer in particular includes inhibiting the migration of cancer cells, suppressing the invasion of cancer cells to other tissues, inhibiting the formation of metastatic cancer cells at a secondary site, suppressing the disassembly dynamic of focal adhesion in the cancer cells, and/or alleviating one or more symptoms of the metastatic cancer. In particular, the term treating includes inhibiting the migration of cancer cells, suppressing the invasion of cancer cells to other tissues, or inhibiting the formation of metastatic cancer cells at a secondary site.

A capping protein Z (CapZ) is a capping protein locating in the Z band of the muscle sarcomere which can cap the barbed end of actin filaments in muscle cells thereby controls the elongation of actin filament. The term "CapZ inhibitor" used herein generally refers to a specific type of compounds that are capable of suppressing the activity of a CapZ, or inhibiting the expression of the CapZ in the cells or a subject. A CapZ inhibitor may be a chemical compound or a nucleic acid molecule that is derived from natural resources, or artificial synthesized. The CapZ inhibitor may bind to a CapZ to exert its inhibitory effect. For instance, the CapZ inhibitor may bind to particularly the CapZ that are recruited on endosomes and/or bridging the early endosomes and actin filaments, and inhibit the release of the CapZ or inhibit the expression or activity of the CapZ, which consequently leading to a cascade of disruption of cellular trafficking in relation to cell movement. It is appreciated in the art that there are two subtypes of capping protein Z, namely capping protein Z alpha (CapZα) and capping protein Z beta (CapZβ). The CapZ inhibitor may be defined by its selectivity towards each subtype of capping protein Z, namely CapZα inhibitor and CapZβ inhibitor.

In an embodiment, the CapZ inhibitor is capable of binding to the CapZβ and locking the CapZ on early endosomes as well as on the barbed ends of actin filaments. On the one hand, the inhibition against CapZ is released from the actin filaments can minimize or prevent filament elongation. On the other hand, the inhibition against CapZ released from early endosomes can stop the transition of the early endosomes into late endosomes, thereby trapping integrin (one of the main components of focal adhesion (FA) complex) within the early endosomes, and inhibiting integrin from being recycling back to cell membrane or being sent to lysosome for degradation. As a result, the turnover/dynamics of FA complex, which is an integrin-containing protein assembly that forms mechanical links between actins and extracellular matrix (ECM), is disrupted, leading to a failure of cell migration. Accordingly, the CapZ inhibitor is useful in inhibiting cell migration, and suitable for use in treating or preventing disorders associated with cell migration.

The inventors found that 6-morpholino-1,3,5-triazine derivatives can act as CapZ inhibitors and are particularly useful in treating metastatic cancer, particularly in treating metastatic breast cancer. The inventors, through their own research, trials, and experiments, found out that 6-morpholino-1,3,5-triazine derivatives modified with a phenylamino group and a hydrozono group are exceptionally suitable for treating metastatic cancer.

In an embodiment, the CapZ inhibitor comprises a structure of Formula (I):

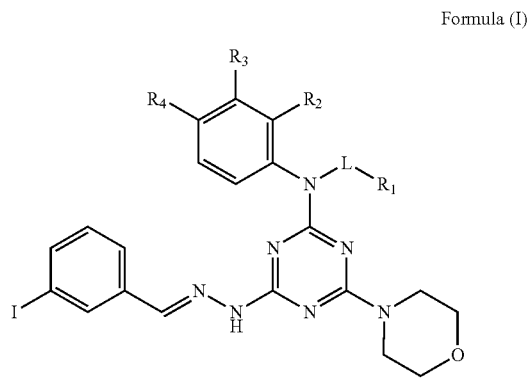

Formula (I)

wherein:

$R_1$, $R_2$, $R_3$ and $R_4$ are independently selected from a hydrogen atom, a saturated or unsaturated C1-C5 alkyl group, a cyano group, a C2-C5 alkoxycarbonyl group, a C5-C8 carbocyclic ring, a C1-C5 alkoxy group, or a halogen atom;

L is a linker group of —$(CH_2)_m$— or —$(CH_2CH_2O)_{m'}$— with m and m' being 0 or any positive integer.

In particular, $R_1$ is selected from a hydrogen atom, a saturated or unsaturated C1-C3 alkyl group, a cyano group, a C2-C5 alkoxycarbonyl group, a C5-C8 carbocyclic ring; $R_2$, $R_3$ and $R_4$ are independently selected from a hydrogen atom, a saturated or unsaturated C1-C3 alkyl group, a C1-C5 alkoxy group, or a halogen atom, wherein each adjacent pair of $R_2$, $R_3$ and $R_4$ may form a fused heterocyclic or carbocyclic ring; and L is a linker group of —$(CH_2)_m$— or —$(CH_2CH_2O)_{m'}$— with m and m' being 0, 1, 2, 3, 4, or 5.

In a preferred embodiment, $R_1$ is a hydrogen atom, a methyl group, a cyano group, an ethynyl group, an ethoxycarbonyl group, or a phenyl group; $R_2$ and $R_3$ are independently a hydrogen atom, a methoxy group, or an ethoxycarbonyl group; $R_4$ is a hydrogen atom, a chloro or a fluoro group; and L is a linker group of —$(CH_2)_m$— or —$(CH_2CH_2O)_{m'}$— with m being 0, 3, 4 or 5, and m' being 0 or 2.

In another preferred embodiment, $R_1$ is a hydrogen atom, a methyl group, a cyano group, an ethynyl group, an ethoxycarbonyl group, or a phenyl group; $R_2$ and $R_3$ together form a fused 6-membered aromatic carbocyclic ring; $R_4$ is a hydrogen atom, a chloro or a fluoro group; and L is a linker group of —$(CH_2)_m$— or —$(CH_2CH_2O)_{m'}$— with m being 0, 3, 4 or 5, and m' being 0 or 2.

In a more preferred embodiment, the CapZ inhibitor comprises a structure of Formula (II):

Formula (II)

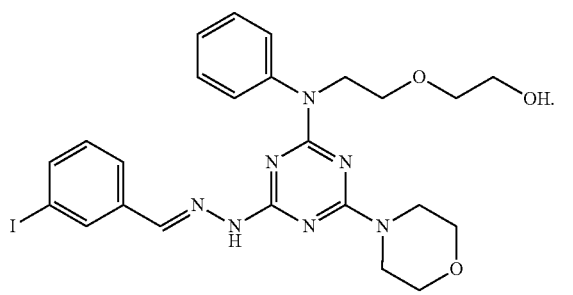

The compound of Formula (II) is also known as 6J-1. This compound may be prepared or obtained according to suitable methods.

The term "subject" used herein refers to an animal or a human, in particular a mammal and most preferably a human. I.e. the subject is in most preferred embodiments a human suffering from a cancer or a metastatic cancer. The subject may also be a cancer patient at risk for metastasis.

The expression "effective amount" generally denotes an amount sufficient to produce therapeutically desirable results, wherein the exact nature of the result varies depending on the specific condition which is treated. The compound of the present invention may be contained in a composition, in particular the pharmaceutical composition, in an effective amount, i.e. an amount suitable to treat or prevent the metastatic cancer or inhibit the metastasis of cancer cells in a subject, in particular a mammal, which also depends on the frequency and number of compositions to be administered. In an embodiment, the compound of the present invention may be administered to a subject at a concentration of about 2 M or 2.5 mg/kg or above. In other embodiment, the compound may be administered at a concentration of about 2.5 mg/kg, 5 mg/kg, 10 mg/kg, 15 mg/kg, 20 mg/kg, 25 mg/kg, or 30 mg/kg.

When the compound is provided in a pharmaceutical composition to a subject, the skilled person is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition.

In an embodiment, the compound of the present invention may be used in combination with one or more chemotherapy drugs. Preferably, the chemotherapy drug may be selected from doxorubicin, taxol, 5-Fu, or temirolimus. A person skilled in the art is able to include other therapeutic compounds which are useful to alleviate the conditions of the subject.

The chemotherapy drug(s) may be administered before, after or simultaneously with the CapZ inhibitor, in particular before or simultaneously with the CapZ inhibitor, further preferred simultaneously with the CapZ inhibitor.

The CapZ inhibitor according to the present invention may be administered by an oral, injective, rectal, topical, parenteral, transdermal or inhalative route to a subject. In an embodiment where the subject is a mouse, the CapZ inhibitor is administered through oral delivery or injection to the subject. The term injection encompasses intraperitoneal, intravenous, intramuscular, subcutaneous and intradermal administration.

In another aspect, the present invention pertains to a method of inhibiting metastasis of cancer cells. The method comprises administering an effective amount of a CapZ inhibitor as described above.

The CapZ inhibitor may be contacted with the cancer cells in combination with one or more chemotherapy drug. Preferably, the chemotherapy drug may be selected from doxorubicin, taxol, 5-Fu, or temirolimus. A person skilled in the art is able to include other suitable therapeutic compounds according to the types of cancer cells.

The cancer cells may be selected from the group consisting of bladder cancer, breast cancer, colon cancer, kidney cancer, lung cancer, ovary cancer, skin cancer, pancreatic cancer, prostate cancer, liver cancer and bone cancer.

In particular, the cancer cells are breast cancer cells, liver cancer cells or lung cancer cells. Preferably, the cancer cells are breast cancer cells.

In embodiments, the compound is contacted with the cancer cells at a concentration of about 0.1 µM or above, in particular at a concentration of about 0.1 µM, about 0.5 µM, about 1 µM, about 5 µM about 10 µM or about 20 µM. In a particular embodiment, the compound is contacted with the cancer cells at a concentration of 1-20 µM.

Accordingly, it is believed that the compound as disclosed in the present invention is capable of treating metastatic cancer, and/or inhibiting the migration and invasion of cancer cells. Thus, the present invention also pertains to a method of preventing metastasis in a cancer patient at risk for metastasis. In particular, the method includes administering an effective amount of the CapZ inhibitor having a structure of Formula (I) to the patient with step(s) as described above.

It would be appreciated that the present invention also pertains to use of a CapZ inhibitor as described above in inhibiting migrations of cancer cells, preferably the cancer cells are metastatic cancer cells, as well as use of a CapZ inhibitor as described above for treating metastatic cancer. Alternatively, there is also provided use of a CapZ inhibitor as described above for the manufacture of a medication for treating metastatic cancer.

The experiments as described below further support the anti-metastatic effect of the CapZ inhibitor according to the present invention.

EXAMPLES

Example 1

The Effect of V1 as an Endosomal Trafficking Inhibitor

Since endosomal trafficking is closely related to metastasis of malignant tumors, the anti-migration effects of V1, a 6-morpholino-1,3,5-triazine derivative, in several human or mouse breast cancer cell lines, e.g. 4T07, 4T1, and MDA-MB-231 were investigated.

Figure 1B:
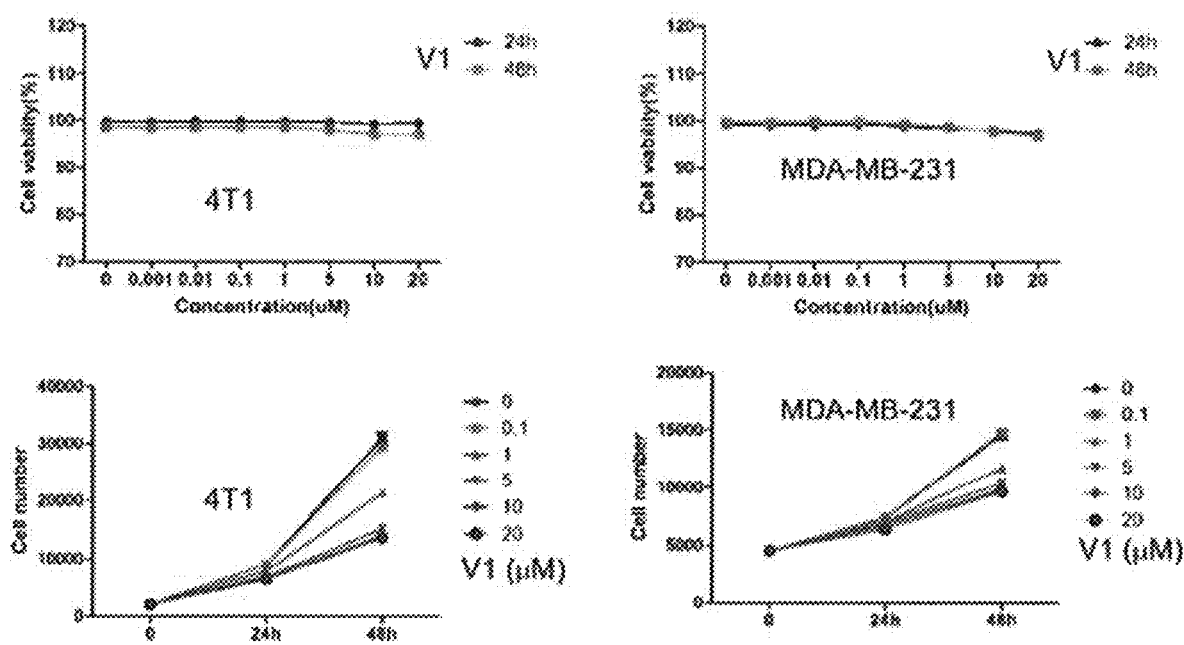
FIG. 1B is a series of line charts showing the cell viability of 4T1, and MDA-MB-231 cells treated with or without V1, at indicated concentrations for 24 or 48 h.
Figure 2A:
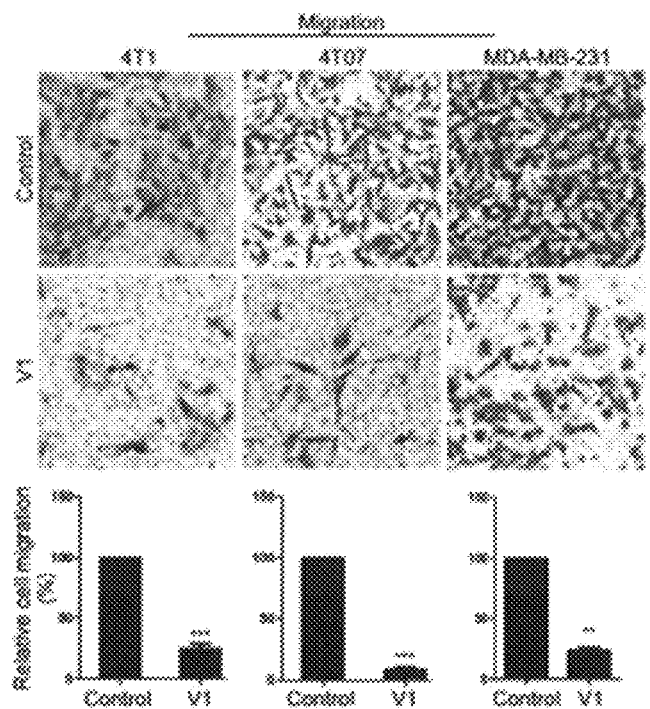
FIG. 2A is a series of microscopic images and bar charts showing the migration of 4T1, 4T07, and MDA-MB-231 cells in transwell plates in the presence or absence of V1 (1 μM).
Figure 2B:
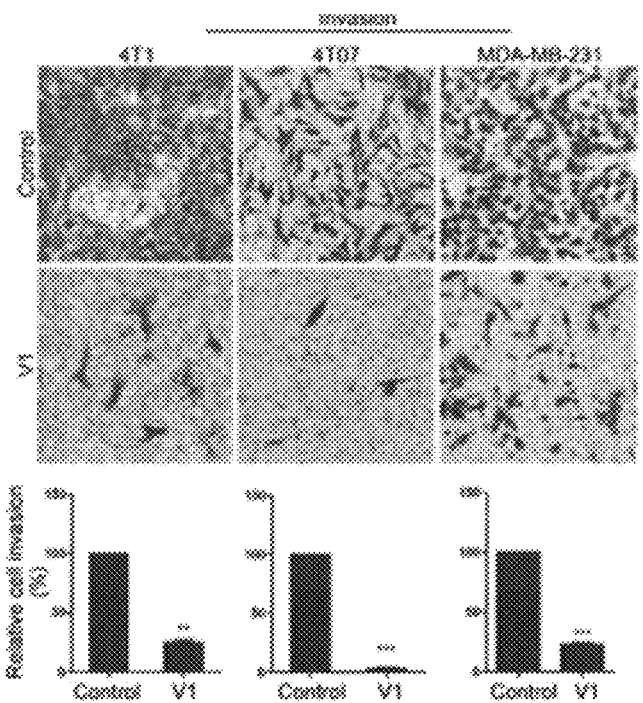
FIG. 2B is a series of microscopic images and bar charts showing the invasion of 4T1, 4T07, and MDA-MB-231 cells in invasion chambers in the presence or absence of V1 (1 μM).
Figure 2C:
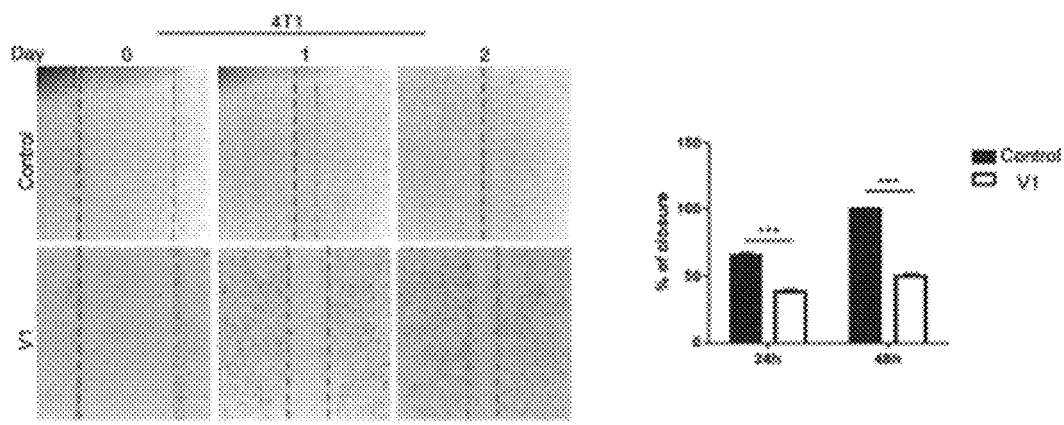
FIG. 2C is a series of optical images and a bar chart showing the closure of a scratch-wound plated with 4T1 cells, treated with or without V1 (1 μM), after 0, 24, and 48 h.
Figure 2D:
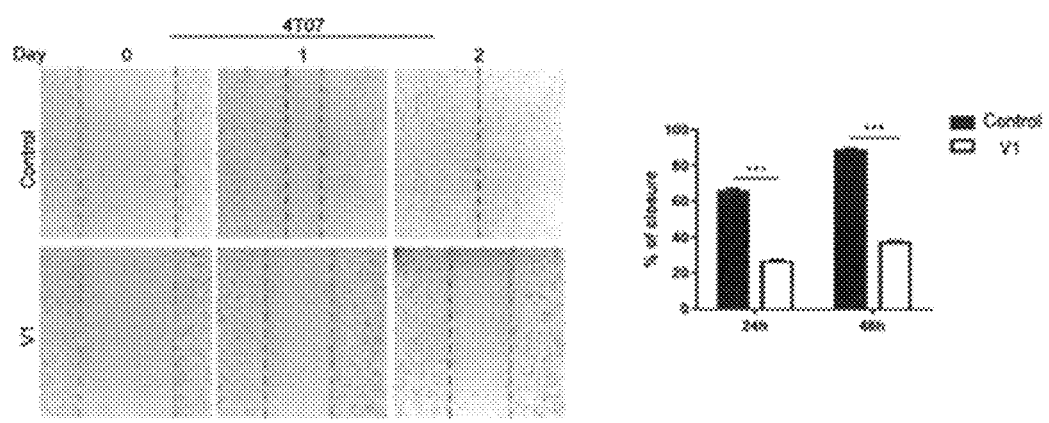
FIG. 2D is a series of optical images and a bar chart showing the closure of a scratch-wound plated with 4T07 cells, treated with or without V1 (1 μM), after 0, 24, and 48 h.
Figure 2E:
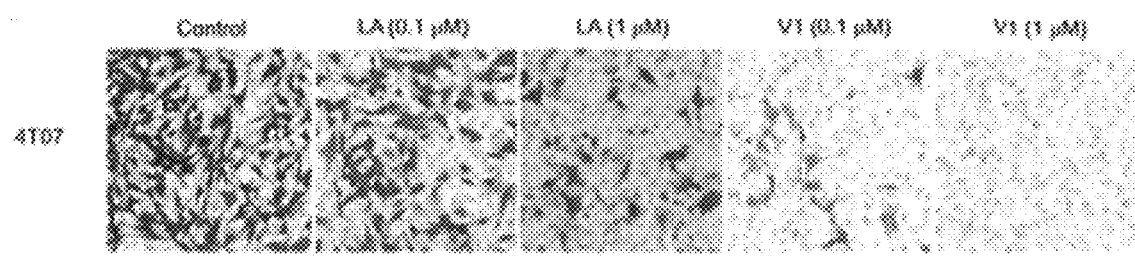
FIG. 2E is a series of microscopic images showing the migration of 4T07 cells in transwell plates in the presence or absence of V1 or LA at indicated concentrations after 18 h.
Figure 2F:
FIG. 2F is the mappings of live-cell imaging that track the movement (in terms of distance and speed) of 4T07 and MDA-MB-231 cells for 12 h at 30 min interval, and the stock charts thereof. The cells were treated with or without V1 (1 μM) for 1 h prior to the imaging.

In this example, the cytotoxicity and the anti-migration effects of V1 are compared with latrunculin A (LA), an F-actin destabilizer. As shown in FIGS. 1A and 1B, V1 exhibited a much lower cytotoxicity than LA. The migration and invasion of the breast cancer cells treated with V1 were investigated by trans-well migration assay, wound-healing assay, and matrigel invasion assays. The breast cancer cells were placed on the upper chamber of the transwell plates or invasion chambers coated with Matrigel in the presence or absence of V1, after 18 h of incubation, the cells at the lower chamber were stained with crystal violet and quantified. As shown in FIGS. 2A-2D, V1 markedly inhibited the migration and invasion of the breast cancer cells in these assays. The anti-migration effect of V1 on 4T07 cells was further compared with LA. As shown in FIG. 2E, it is found that LA exhibited a much lower effect on the migration of 4T07 cells at similar concentrations of V1. It is also confirmed by live cell mobility tracking of cells treated with or without V1, at 30 min interval, that V1 significantly inhibited the speed and distance of cell movement (FIG. 2F). These data indicate that V1 is an effective anti-migration agent in vitro.

Example 2

The Effect of V1 on Cancer Cell Migration and Invasion

Figure 3A:
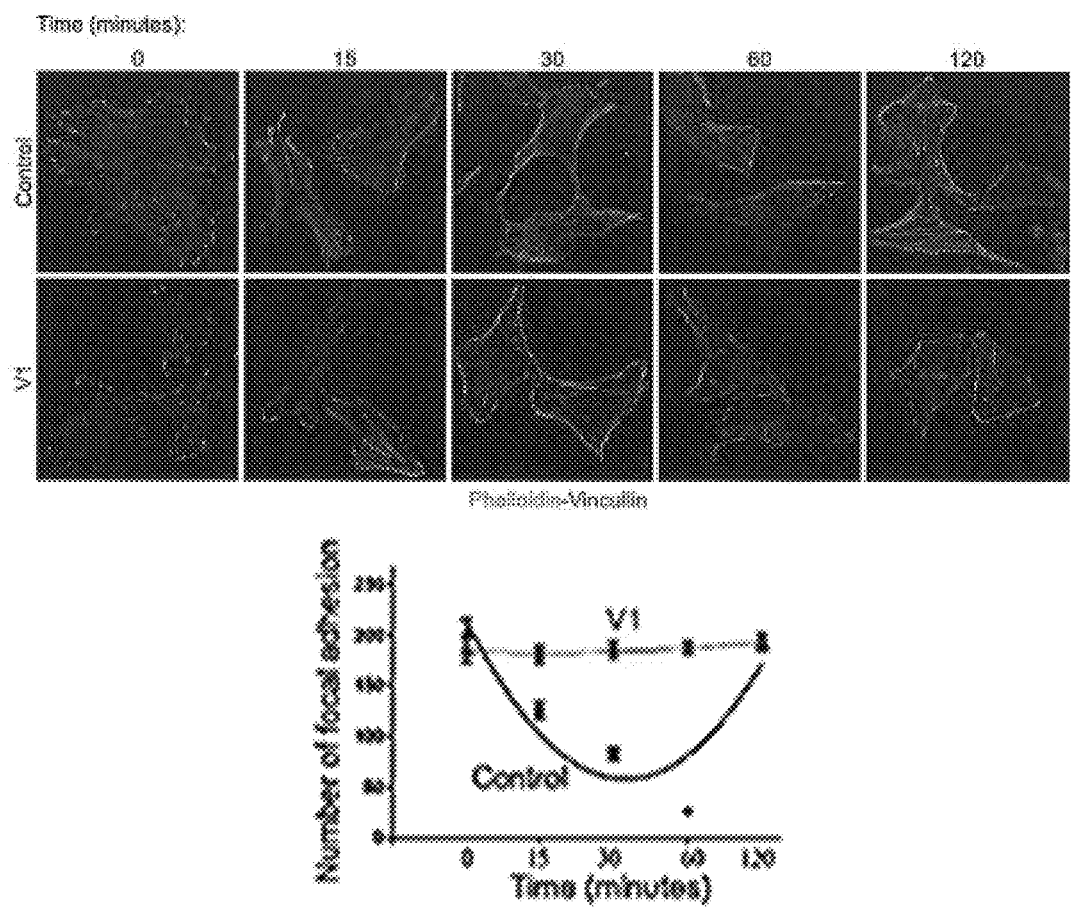
FIG. 3A is a series of microscopic images showing the co-localization between Phalloidin and Vinculin of HeLa cells treated with nocodazole (NOC) in the presence or absence of V1 (1 μM), and a line chart showing the number of focal adhesion of said HeLa cells. The indicated time points represent at which NOC was removed from the HeLa cells, followed by staining the cells with anti-Vinculin antibody and Phalloidin.

Focal adhesion (FA) dynamics is a key process during cell migration and therefore the effects of V1 treatment on spatiotemporal regulation of FA dynamics have been assessed. HeLa cells were plated on cover slides at 24-well plates and treated with nocodazole (NOC) in the presence or absence of V1 (1 µM). At indicated times, after removing NOC, the cells were stained with anti-Vinculin antibody and Phalloidin, and the Vinculin puncta were quantified. As shown in FIG. 3A, the punctate staining pattern of Vinculin (a cytoplasmic actin-binding protein enriched in FA) indicates that treatment of the cells with NOC depolymerized the microtubules and stabilized the formation of FAs. The removal of NOC led to microtubule regrowth, which resulted in a decreasing number of FAs in a time-dependent manner until the reformation of FAs (top panel of FIG. 3A). V1 treatment markedly inhibited FA disassembly, as shown by the continuous localization of Vinculin puncta after NOC release (bottom panel of FIG. 3A). These data demonstrate that V1 compromises the assembly-disassembly dynamics of FAs, which may be associated with the inhibitory effect of V1 on of the migration and invasion of tumor cells.

During cell migration, integrin are internalized, degraded, and recycled back to the plasma membrane to control the dynamic assembly/disassembly of the FA complex between the migrating cells and the extracellular matrix. The effect of V1 on integrin recycling and/or degradation was examined by integrin immunostaining. HeLa cells were plated on cover slides at 24-well plates and treated with or without V1 (1 µM), followed by incubation with an anti-integrin antibody on ice for 1.5 h. The cells were released from cold arrest at indicated times and stained with antibodies against EEA1 or LAMP1.

Figure 3B:
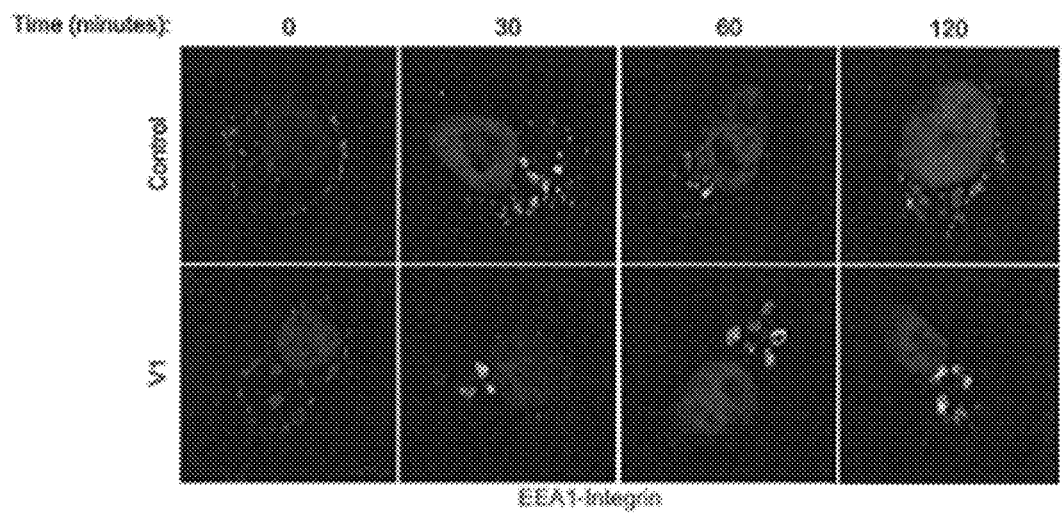
FIG. 3B is a series of microscopic images showing the co-localization between anti-integrin and EEA1 of HeLa cells treated with or without V1 (1 μM).
Figure 3C:
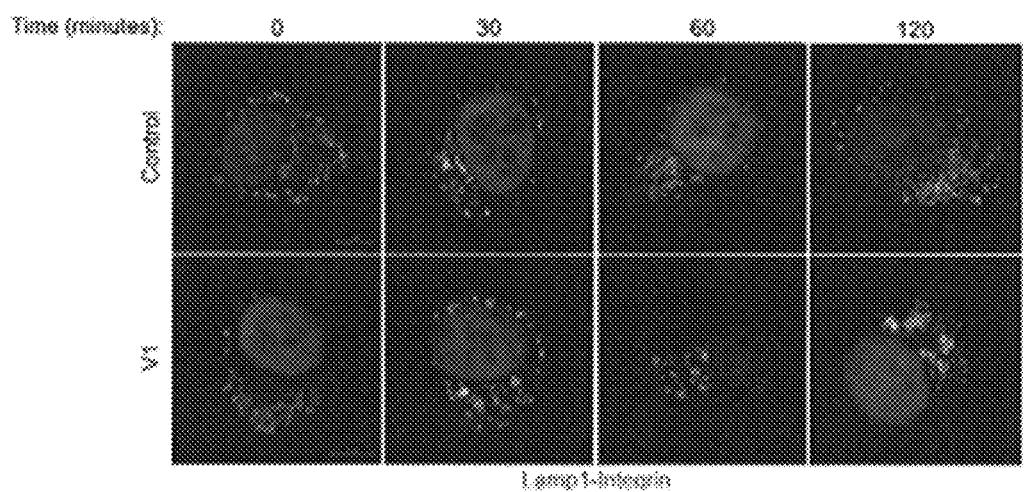
FIG. 3C is a series of microscopic images showing the co-localization between anti-integrin and LAMP1 of HeLa cells treated with or without V1 (1 μM). The indicated time points of FIGS. 3B and 3C represent at which the HeLa cells were released from cold arrest, followed by being stained with antibodies against EEA1 or LAMP1.

In control cells, the integrin-antibody complex was re-localized from the cell membrane to the early endosomes by 30 min to 60 min, as manifested by the co-localization between integrin and EEA1 (an early endosomal marker) (top panel of FIG. 3B). The internalized integrin-antibody was either sent to lysosome for degradation, as manifested by the co-localization between integrin and LAMP1 (a late endosome/lysosome marker) (top panel of FIG. 3C), or were recycled back to the cell membrane by 2 h (top panels of FIGS. 3B and 3C). In contrast, the integrin-antibody complex was trapped in the early endosomes in V1-treated cells, and failed to be recycled back to the cell membrane or sent to the lysosome for degradation (bottom panels of FIGS. 3B and 3C). In summary, these data indicate that V1 inhibits the dynamics of integrin recycling and degradation, and this is likely to contribute to the defects in FA turnover and lead to the inhibition of migration and invasion of tumor cells.

Figure 4A:
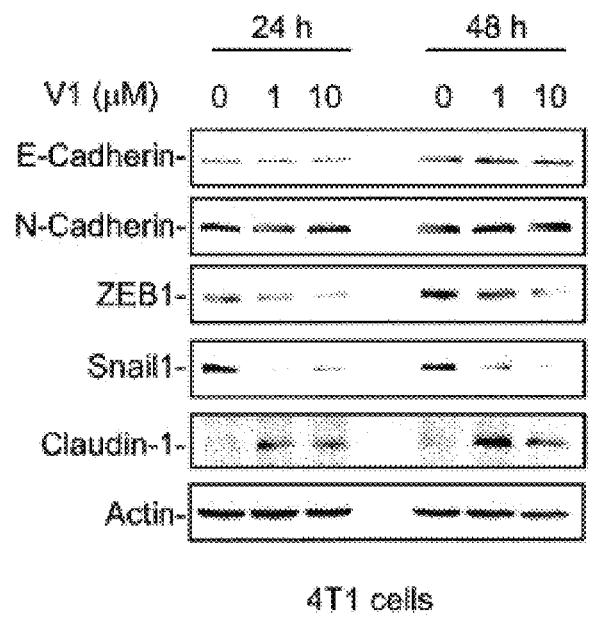
FIG. 4A is an immunoblot showing the expression levels of EMT genes of 4T1 cells treated with or without V1 at indicated concentrations for 24 or 48 h.
Figure 4B:
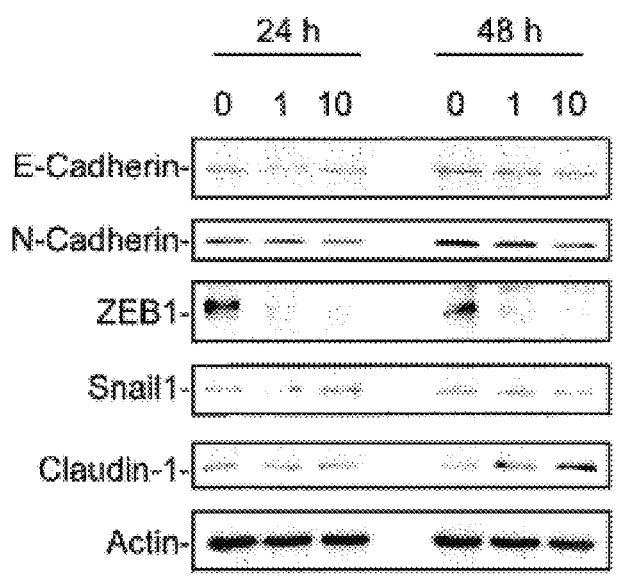
FIG. 4B is an immunoblot showing the expression levels of EMT genes of MBA-MD-231 cells treated with or without V1 at indicated concentrations for 24 or 48 h.

In cancer cell invasion, EMT plays an important role therein. Thus, the association between the anti-invasion effect of V1 and EMT was investigated. 4T1 or MDA-MB-231 cells were treated with or without V1 at indicated concentrations for 24 or 48 h, followed by determining the expression levels of EMT via immunoblotting analysis. Interestingly, V1 increased the expression of Claudin-1 and decreased the expression of Snail1 in 4T1 cells (FIG. 4A), but not in MDA-MB-231 cells (FIG. 4B). Similarly, V1 decreased the expression of ZEB1 in MDA-MB-231 cells (FIG. 4B), but not in 4T1 cells (FIG. 4A). In addition, V1 has no effect on the expression of E-Cadherin and N-Cadherin in 4T1 and MDA-MB-231 cells (FIGS. 4A and 4B). Since the switch between E-Cadherin and N-Cadherin is the signature of cancer EMT, these results suggest that V1 does not directly regulate EMT in cancer cells.

Example 2

Anti-Metastasis Effect of V1 on Cancer Cells In Vivo

Figure 5A:
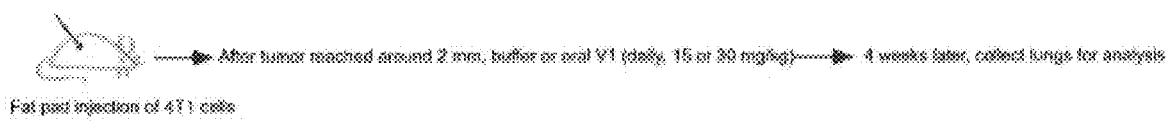
FIG. 5A is a schematic diagram showing a method for determining the anti-metastatic activity of V1 in female nude mice with their fat pads injected with 4T1 cells, where V1 is administered to the mice via an oral gauge.
Figure 5B:
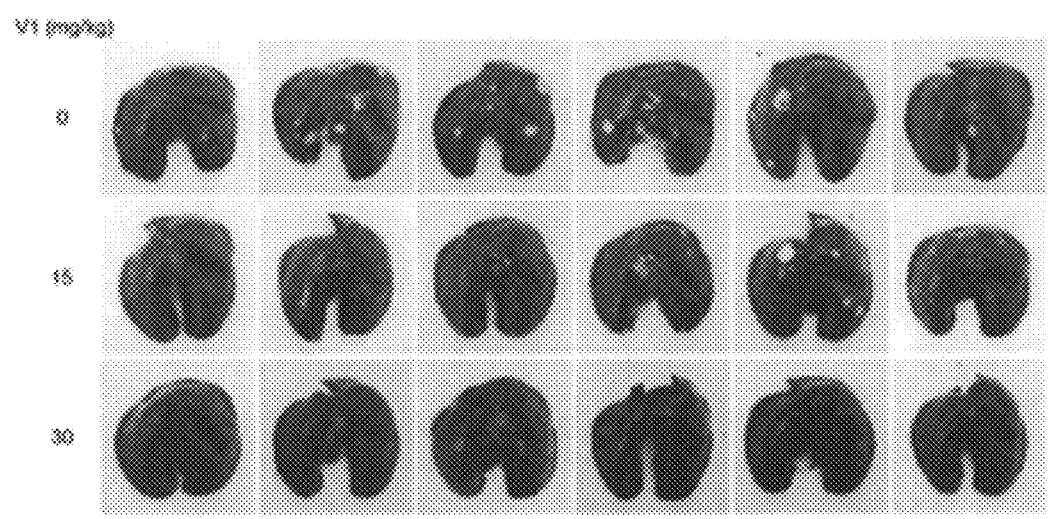
FIG. 5B is a series of optical images showing the excised lungs of the mice treated with a buffer or V1 (15 or 30 mg/kg, daily) via the oral gauge for 4 weeks.
Figure 5C:
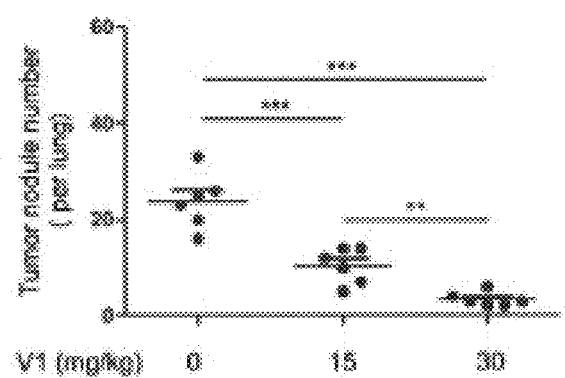
FIG. 5C is a line plot showing the number of tumor nodules in the excised lungs against different concentrations of V1.
Figure 5D:
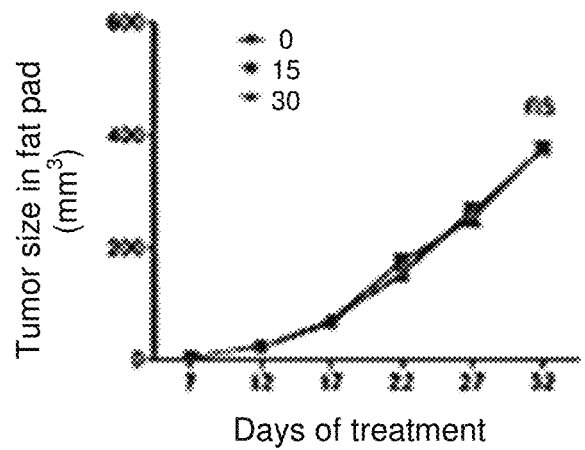
FIG. 5D is a line chart showing the size of primary tumor against days after treatment.
Figure 5E:
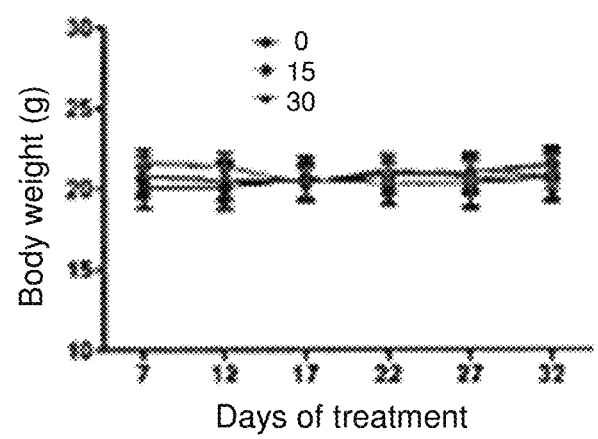
FIG. 5E is a line chart showing the body weight of mice after subjecting to the treatment for different days.
Figure 5F:
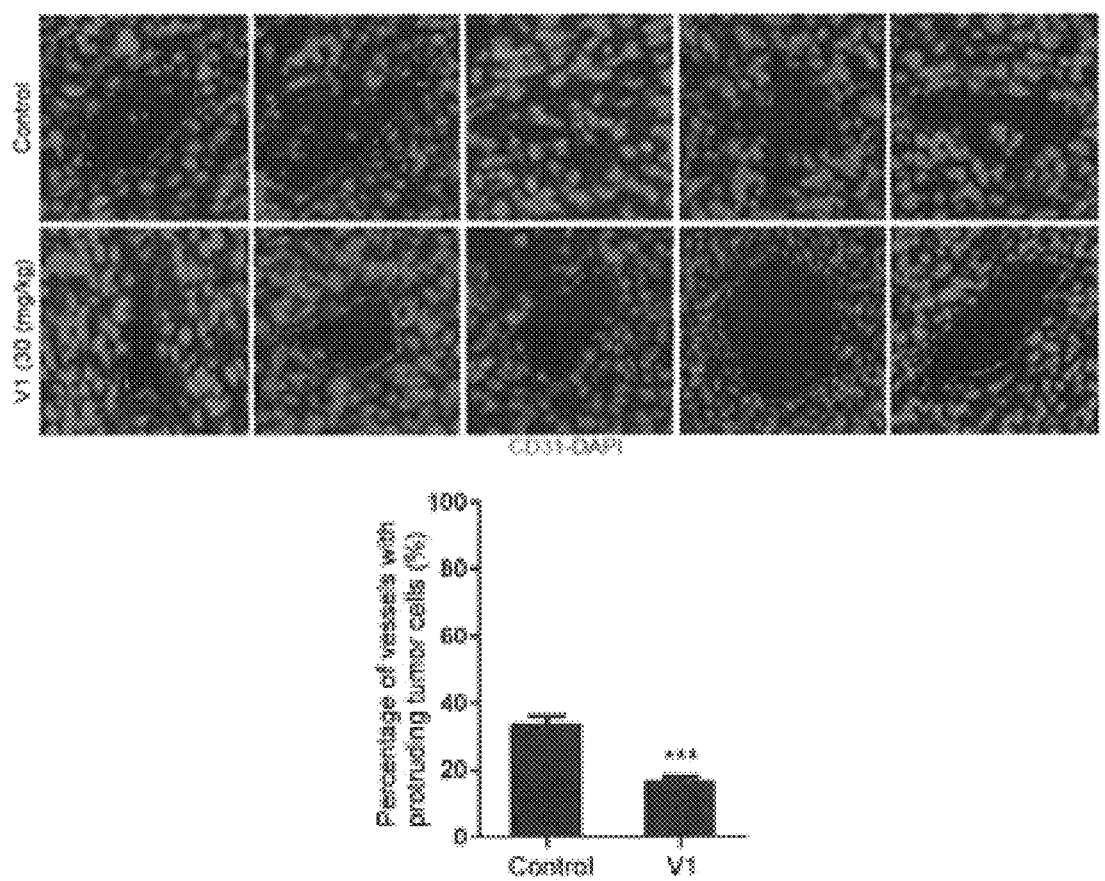
FIG. 5F is a series of microscopic images showing the co-localization between DAPI and anti-CD31 antibody of mammary tumor-bearing tissues, and a bar chart showing the tumor cells inside the vessels of the tissue.

In view of the remarkable inhibitory effect of V1 on the migration and invasion of breast cancer cells (FIGS. 1A and 1B, 2A-2E), V1 was administered to several experimental mouse models to determine its anti-metastatic effect in vivo. First, we studied V1's anti-metastatic effects in a spontaneous cancer mouse model by fat pad injecting 4T1 mouse breast cancer cells into nude mice (FIG. 5A). After tumors were palpable (~5 mm, around day 9), the mice were randomly divided into three groups (six mice per group) orally treated with or without V1 (15 or 30 mg/ml) every day. After 4 weeks, the mice were sacrificed; the primary tumors and lungs of the mice were harvested for analysis. Importantly, V1 significantly inhibited the metastasis of 4T1 cells in the nude mice, manifested by fewer tumor nodules in the lungs of V1-treated groups compared with the control groups (FIGS. 5B and 5C). Notably, V1 did not affect the growth of primary tumor (FIG. 5D), or the mouse weight (FIG. 5E).

Figure 6A:
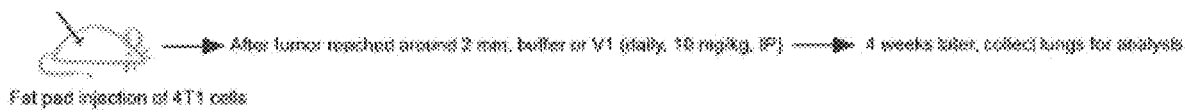
FIG. 6A is a schematic diagram showing a method for determining the anti-metastatic activity of V1 in female nude mice with their fat pads injected with 4T1 cells.
Figure 6B:
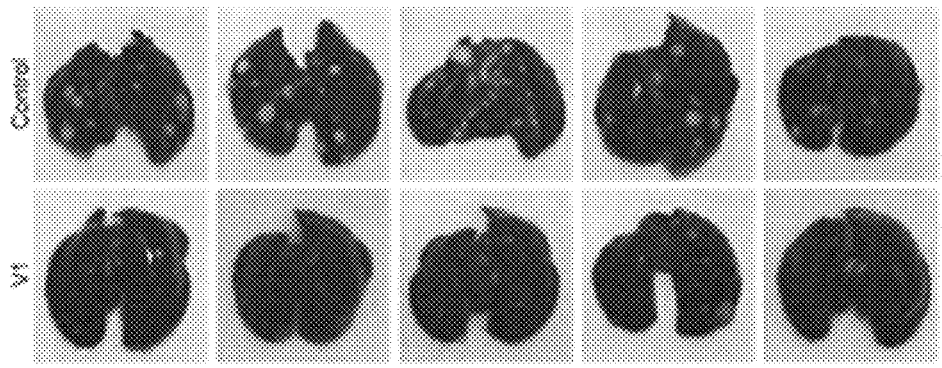
FIG. 6B is a series of optical images showing the excised lungs of the mice treated with a buffer or V1 (10 mg/kg, IP, daily) for 4 weeks.
Figure 6C:
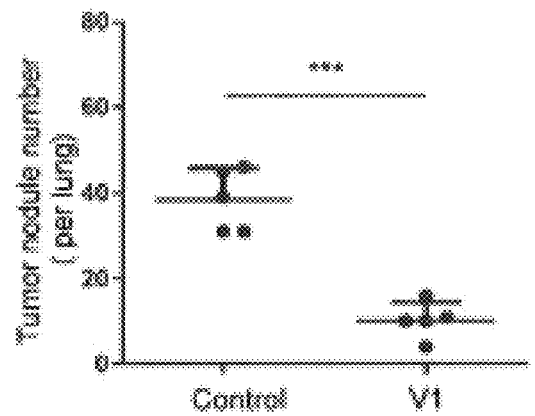
FIG. 6C is a line plot showing the number of tumor nodules in the excised lungs of the mice treated with the buffer or V1.
Figure 6D:
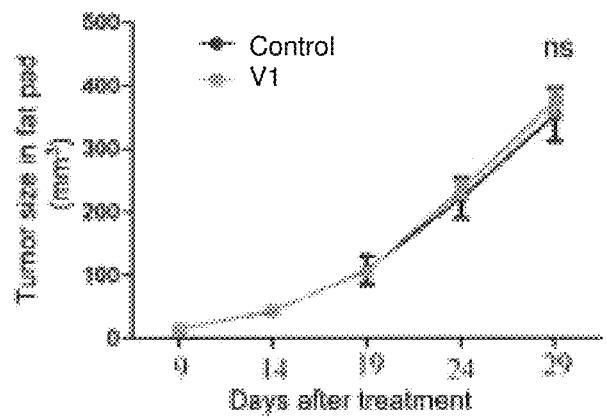
FIG. 6D is a line chart showing the size of primary tumor of the mice against days after treatment.
Figure 6E:
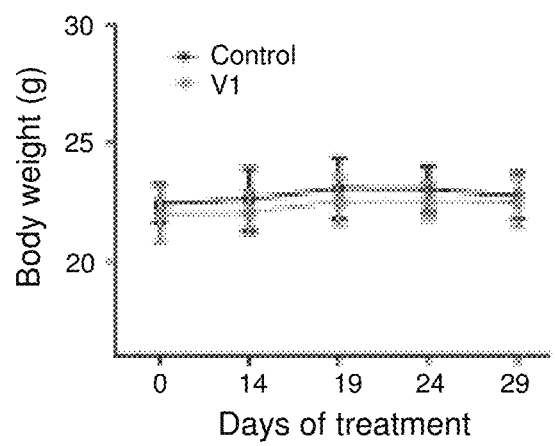
FIG. 6E is a line chart showing the body weight of mice after subjecting to the treatment for different days.
Figure 6F:
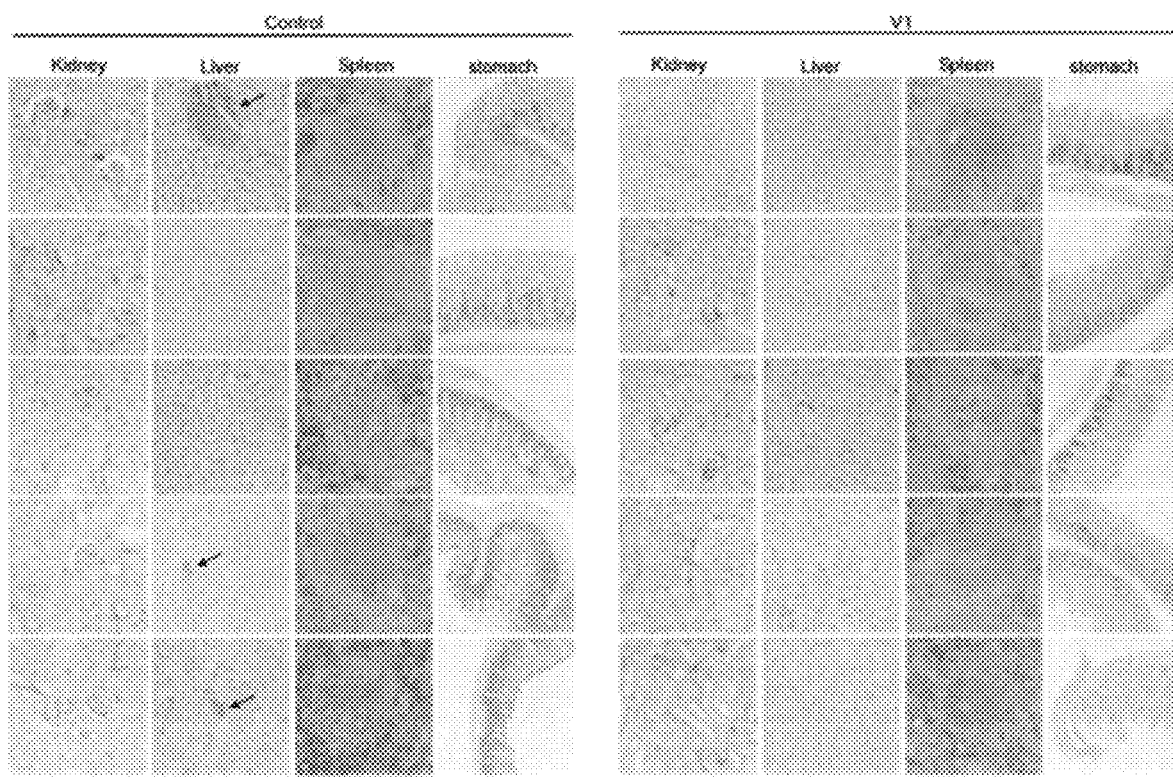
FIG. 6F is a series of histological images showing the metastatic tumor nodules found in the major organs of the mice treated with the buffer or V1.

At the end of experiments, the primary tumor sections were collected and immunostained with CD31 antibody and DAPI to quantify the tumor cells inside the blood vessels of the primary tumor tissue. It is manifest that there were far few tumor cells detected inside tumor tissue's blood vessels in V1-treated group than the control group (FIG. 5E), indicating that V1 significantly inhibits intravasation of primary tumor cells. Similar results were also observed in intraperitoneal (IP) delivery of V1 (10 mg/kg, daily) in this spontaneous cancer mouse model (FIGS. 6A-6E). In addition, the metastatic tumor nodules were found in livers of the control groups, but not in the V1-treated groups (FIG. 6F).

Figure 7A:
FIG. 7A is a schematic diagram showing a method for determining the anti-metastatic activity of V1 in nude mice injected with Fluc-mCherry-expressing 4T07 cells via tail vein injection.
Figure 7B:
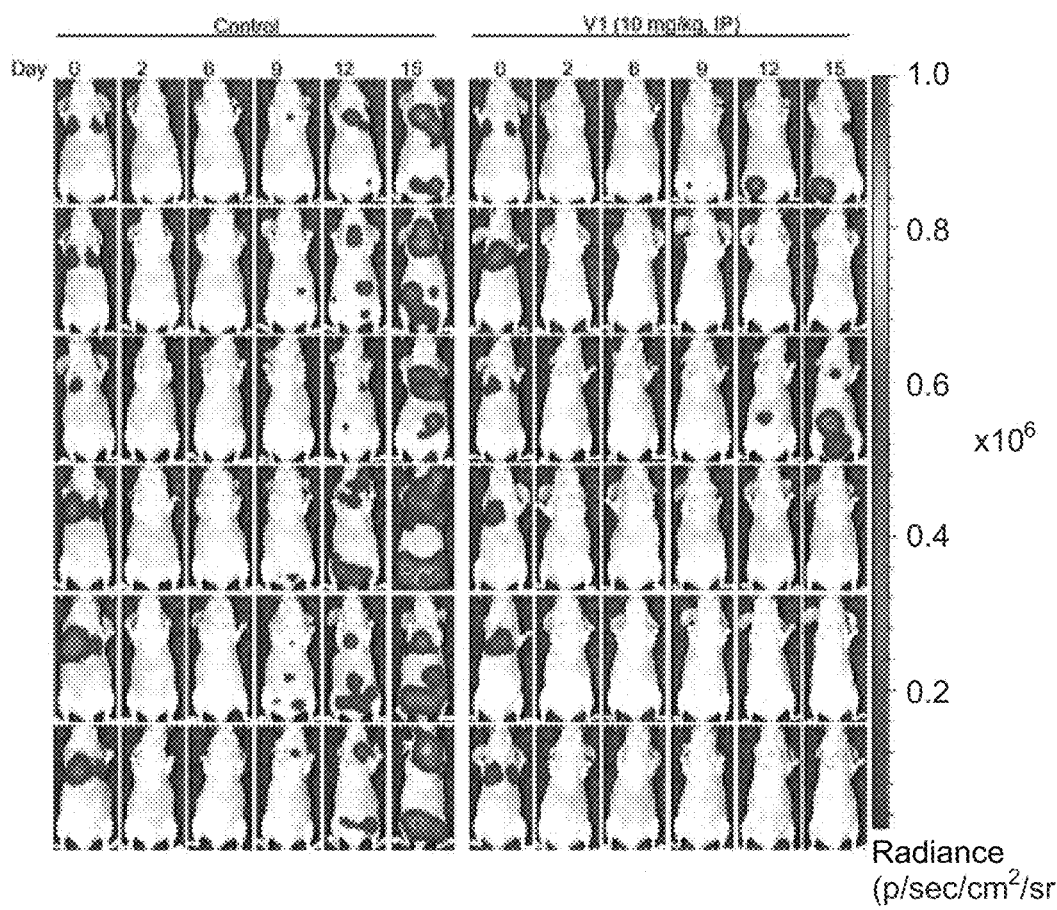
FIG. 7B is a series of luminescence images of the mice treated with or without V1 (10 mg/kg, IP, daily).
Figure 7C:
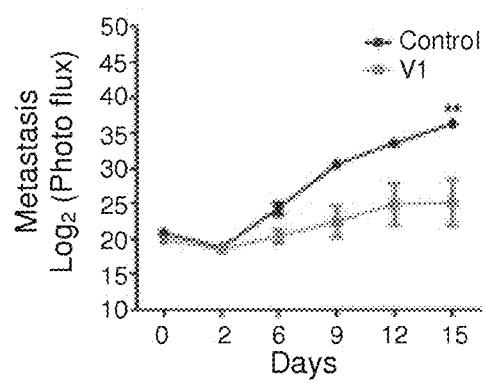
FIG. 7C is a line chart showing the degree of metastasis (in terms of fluorescence signals) against treatment days of the mice of FIG. 7B.

The anti-metastatic effect of V1 in another mouse model was also assessed. Fluc-mCherry-expressing 4T07 mouse breast cancer cells were injected into nude mice by tail vein injection. After 24 h, the mice were randomly divided into two groups (six mice per group) and treated with or without V1 (10 mg/kg, IP, daily) for two weeks (FIG. 7A). During the course of experiment, the mice were imaged every 3-4 days, and the luminescent signals were quantified. As shown in FIGS. 7B and 7C, V1 significantly inhibited the metastasis of 4T07 cells, manifested by much weaker luminescent signals spread over a smaller area in V1-treated mice when compared with control mice during the course of drug treatment. After two weeks, the mice were sacrificed and the major organs, including lungs, livers, etc., were isolated and subjected to fluorescence imaging to detect the spreading condition of the metastatic tumors.

Figure 7D:
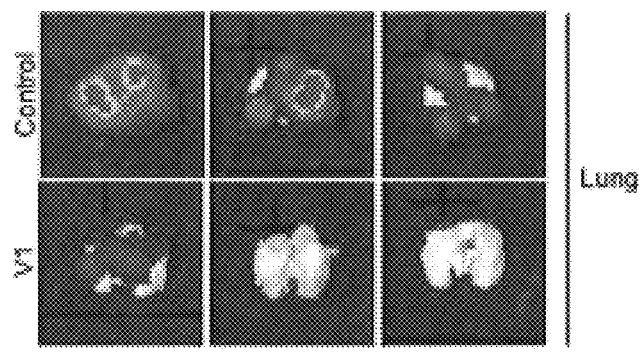
FIG. 7D is a series of luminescence images and a line plot showing the degree of metastasis in lungs of the mice of FIG. 7B.
Figure 7D:
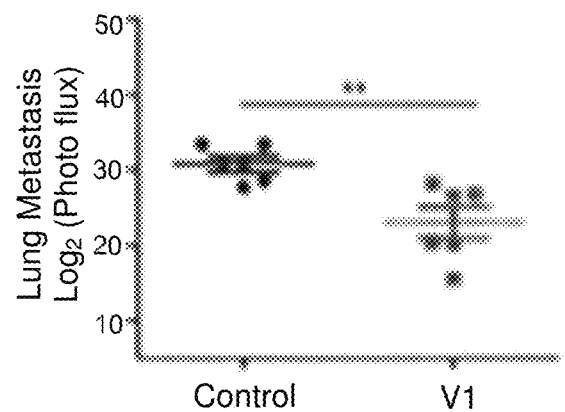
Figure 7E:
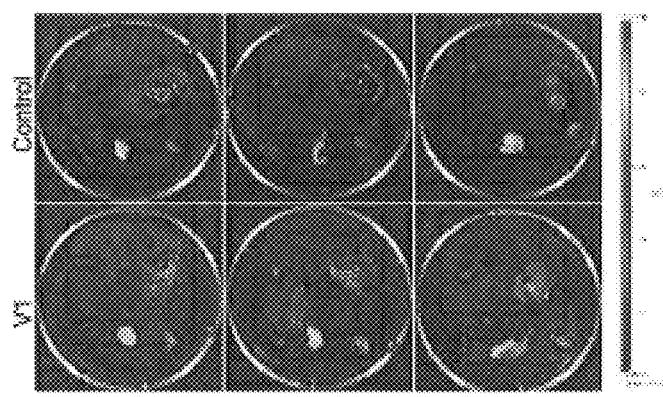
FIG. 7E is a series of luminescence images and a table showing the degree of metastasis in other major organs of the mice of FIG. 7B.
Figure 8A:
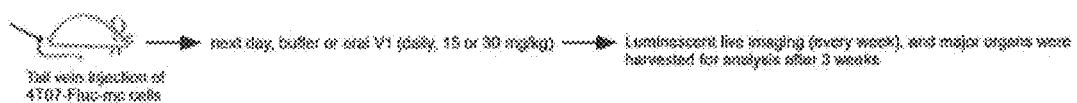
FIG. 8A is a schematic diagram showing a method for determining the anti-metastatic activity of V1 in nude mice injected with Fluc-mCherry-expressing 4T07 cells via tail vein injection.
Figure 8B:
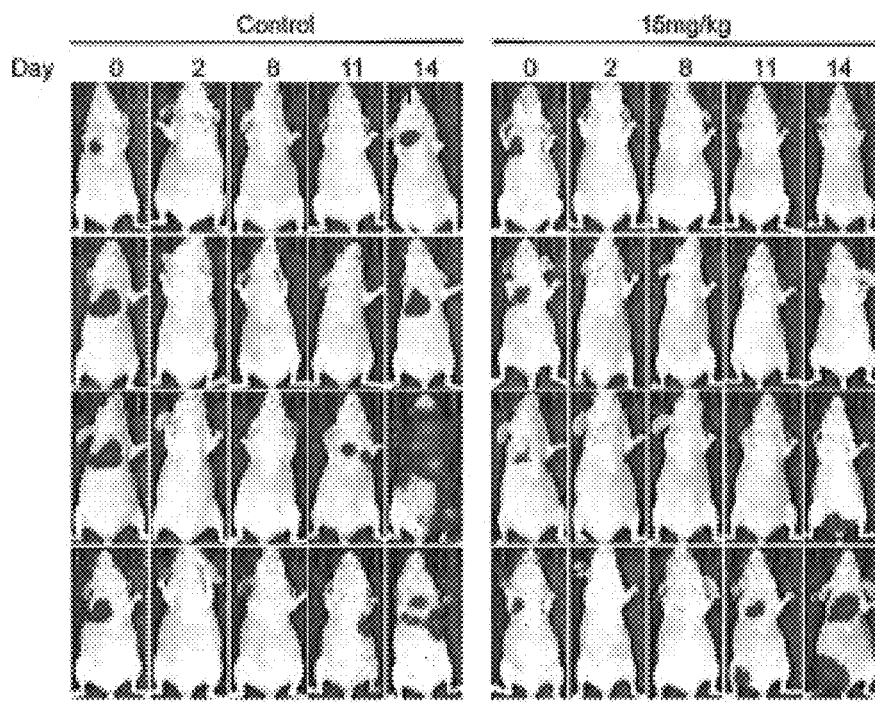
FIG. 8B is a series of luminescence images the mice treated with or without V1 (15 or 30 mg/kg, daily) via an oral gauge for 2 weeks.
Figure 8B:
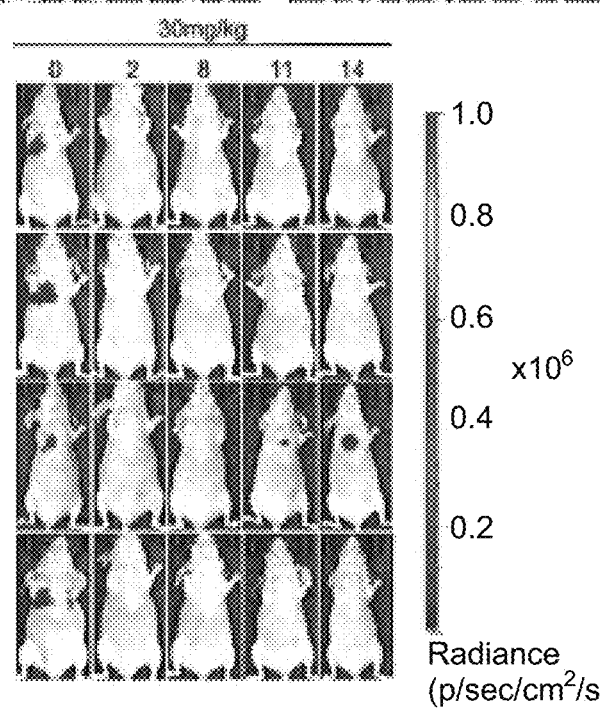
Figure 8C:
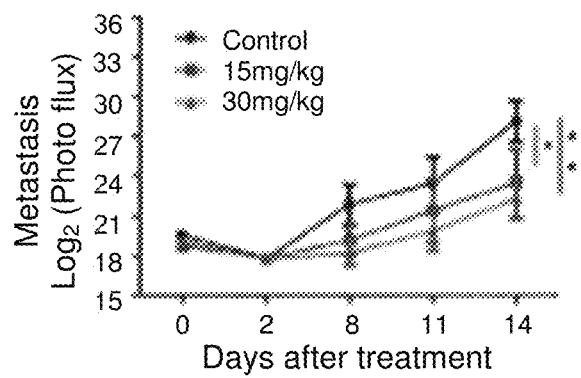
FIG. 8C is a line chart showing degree of metastasis (in terms of fluorescence signals) against treatment days of the mice of FIG. 8B.
Figure 8D:
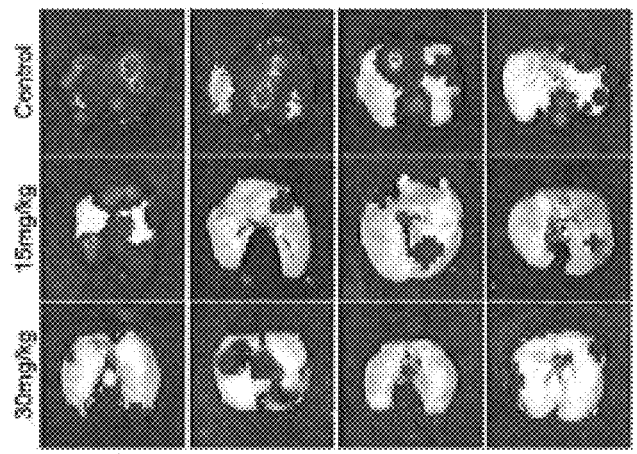
FIG. 8D a series of luminescence images showing the degree of metastasis in lungs of the mice of FIG. 8B.
Figure 8E:
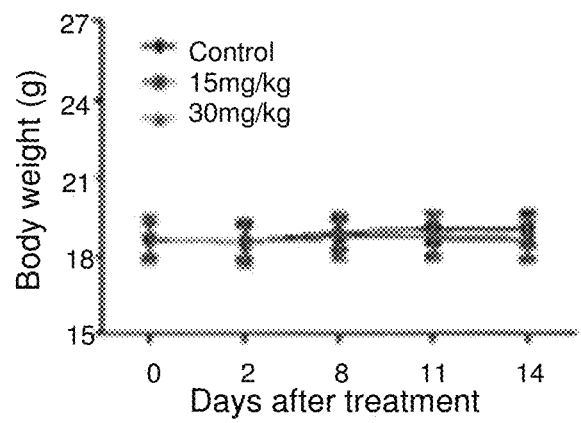
FIG. 8E is a line chart showing the body weight of the mice of FIG. 8B against days of treatment.

Likewise, many organs of the control groups exhibited strong luminescent signals, whereas the organs of V1-treated groups showed much weaker signals (FIGS. 7D and 7E). Similar results were observed in oral delivery of V1 (15 mg/kg or 30 mg/kg, daily) in this experimental metastasis mouse model (FIGS. 8A-8E).

Figure 9A:
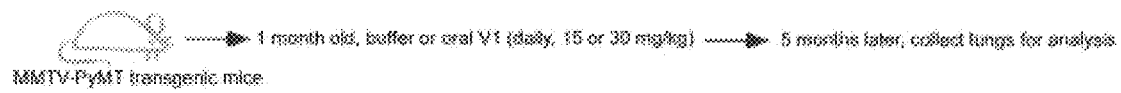
FIG. 9A is a schematic diagram showing a method for determining the anti-metastatic activity of V1 on breast cancer in one-month old female MMTV-PyMT transgenic mice.

In addition to the aforementioned immunodeficient mouse models, the anti-metastatic effect of V1 towards MMTV-PyMT transgenic mice, which have a normal immune system, has been assessed. In one-month old female MMTV-PyMT mice, the mammary gland-specific expression of PyMT results in the development of mammary adenocarcinomas and metastatic lesions in lymph nodes and lungs. After the adenocarcinoma development, the mice were randomly divided into three groups (six mice per group) and treated with V1 (15 mg/kg or 30 mg/kg, oral, daily) for 3 months. At the end of experiment, the lungs of each group of mice were collected and subjected to H&E staining. The tumor nodules in each lung, the number of mammary bearing tumors, and the weight of tumors were quantified (FIG. 9A).

Figure 9B:
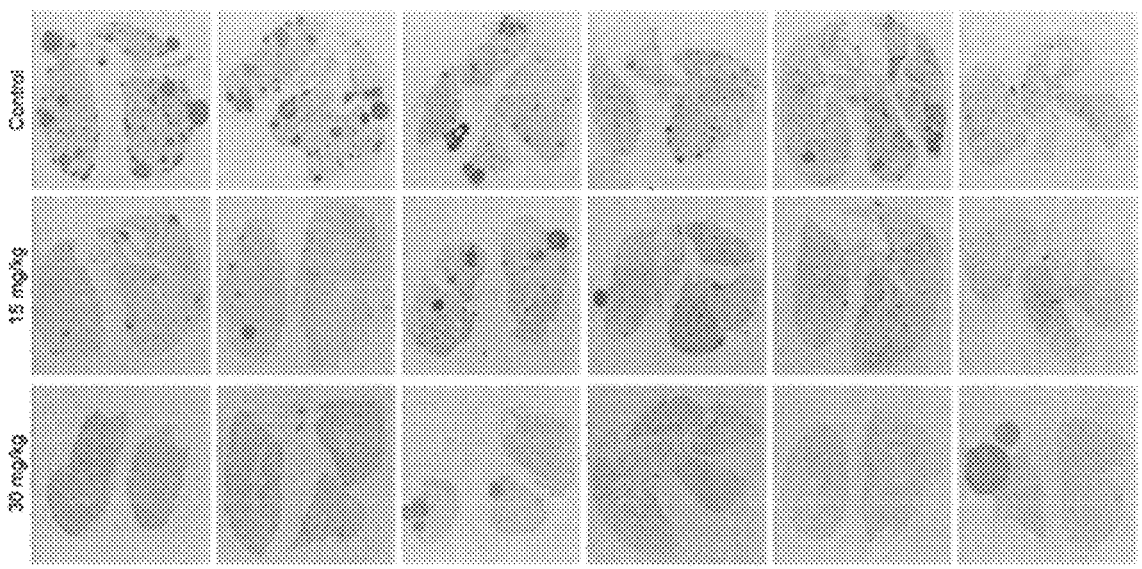
FIG. 9B is a series of histological images showing the metastatic tumor nodules found in the lungs of the mice treated with a buffer or V1 (15 or 30 mg/kg, daily) via an oral gauge for 3 months.
Figure 9C:
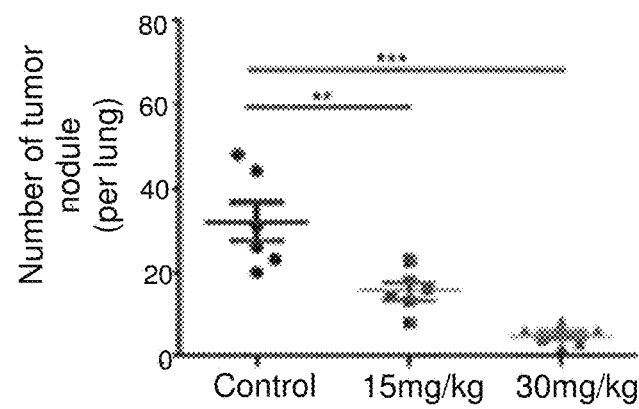
FIG. 9C is a line plot showing the number of tumor nodules in the lungs of the mice of FIG. 9B.
Figure 9D:
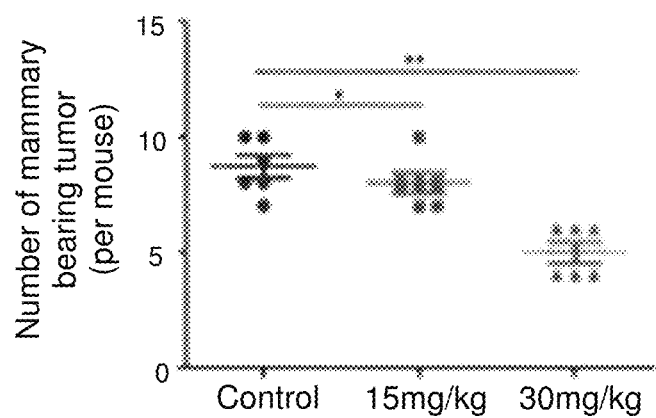
FIG. 9D is a line plot showing the number of mammary bearing tumor in the mice treated with or without V1.
Figure 9E:
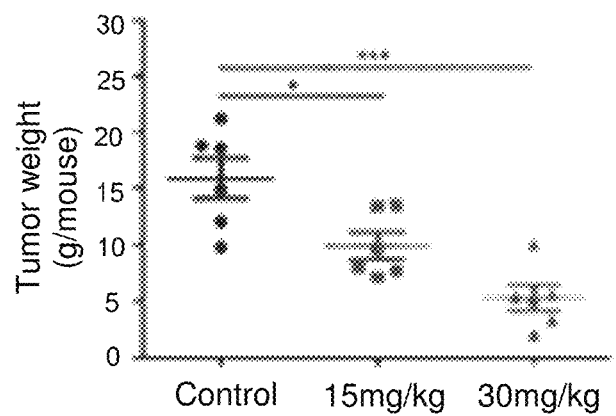
FIG. 9E is a line plot showing the weight of mammary tumor in the mice treated with or without V1.
Figure 10A:
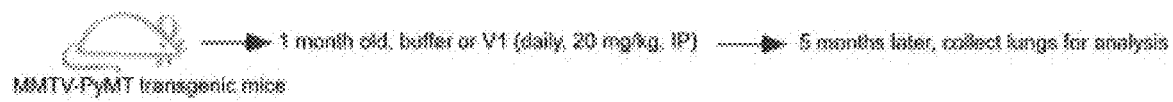
FIG. 10A is a schematic diagram showing a method for determining the anti-metastatic activity of V1 on breast cancer in one-month old female MMTV-PyMT transgenic mice.
Figure 10B:
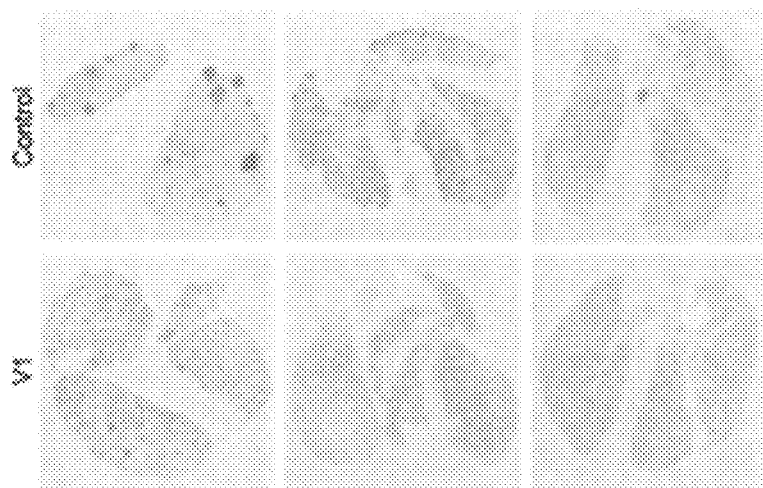
FIG. 10B is a series of histological images showing the metastatic tumor nodules found in the lungs of the mice treated with a buffer or V1 (20 mg/kg, daily) via IP injection for 5 months.
Figure 10C:
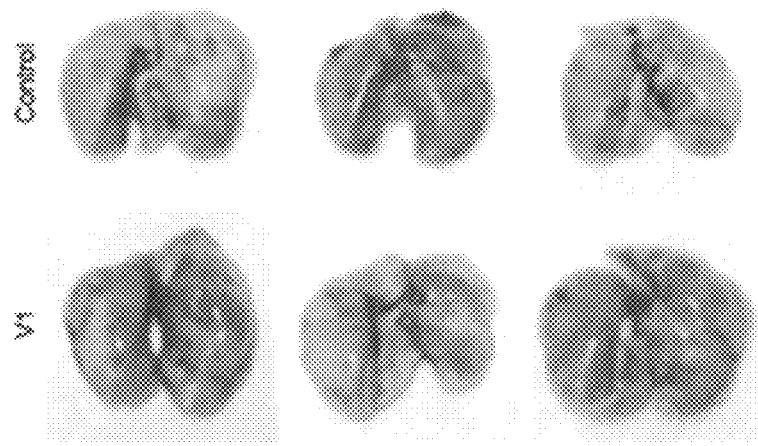
FIG. 10C is a series of optical images showing the excised lungs of the mice treated with or with V1.
Figure 10D:
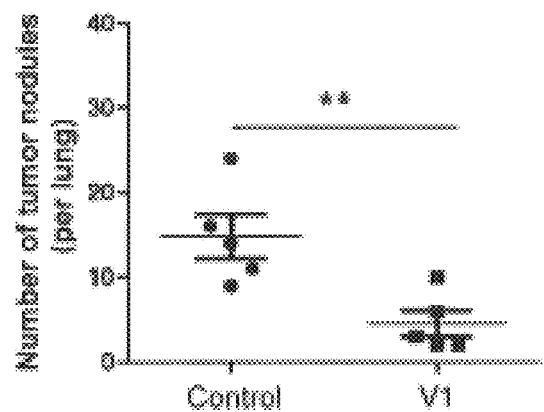
FIG. 10D is a line plot showing the number of tumor nodules in the lungs of FIG. 10B.
Figure 10E:
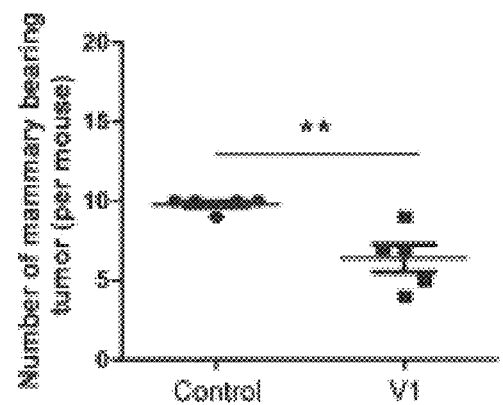
FIG. 10E is a line plot showing the number of mammary bearing tumor in the mice treated with or without V1.
Figure 10F:
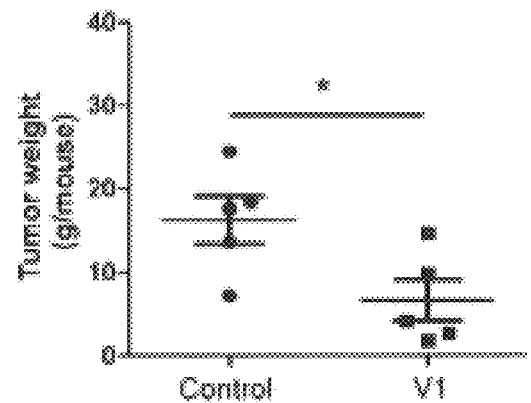
FIG. 10F is a line plot showing the weight of mammary tumor in the mice treated with or without V1.

Likewise, V1 treatment significantly decreased the number of tumor nodules in the mice lungs (FIGS. 9B and 9C). Interestingly, V1 treatment also significantly decreased the number of mammary bearing tumors (FIG. 9D) and the weight of mammary tumors (FIG. 9E). Similar results were observed in IP delivery of V1 (20 mg/kg, daily) in this transgenic mouse model (FIGS. 10A-10F).

Example 3

Figure 11A:
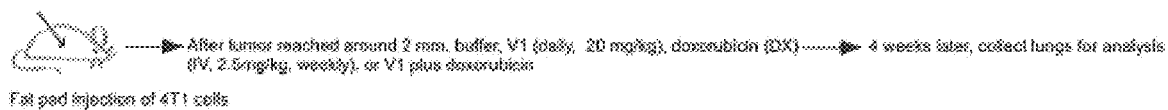
FIG. 11A is a schematic diagram showing a method for determining the anti-metastatic activity of V1 in combination with doxorubicin (DX) in female nude mice with their fat pads injected with 4T1 cells.
Figure 11B:
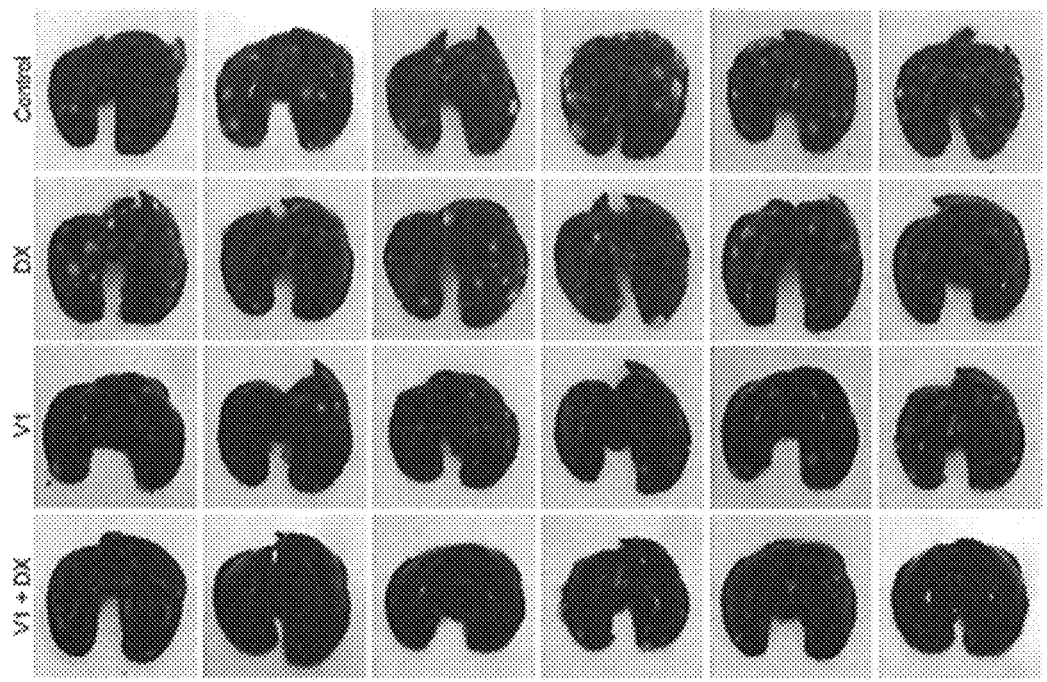
FIG. 11B is a series of optical images showing the excised lungs of the mice treated with a buffer, V1 (20 mg/kg, IP, daily), DX (2.5 mg/kg, IV, daily), or V1 plus DX for 4 weeks.
Figure 11C:
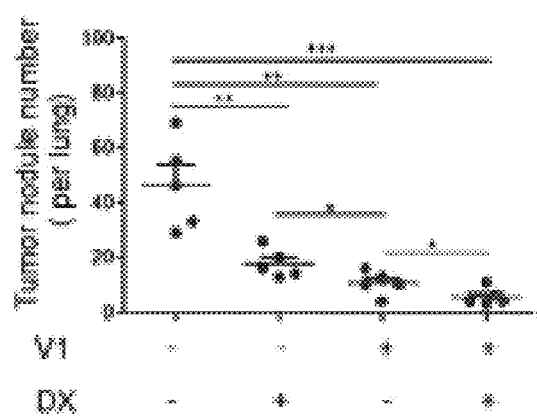
FIG. 11C is a line plot showing the number of tumor nodules in the excised lungs of the mice of FIG. 11B.
Figure 11D:
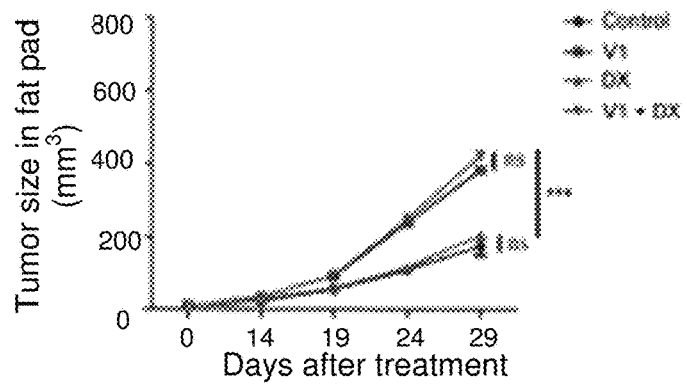
FIG. 11D is a line chart showing the size of primary tumor of the mice against days after treatment.
Figure 11E:
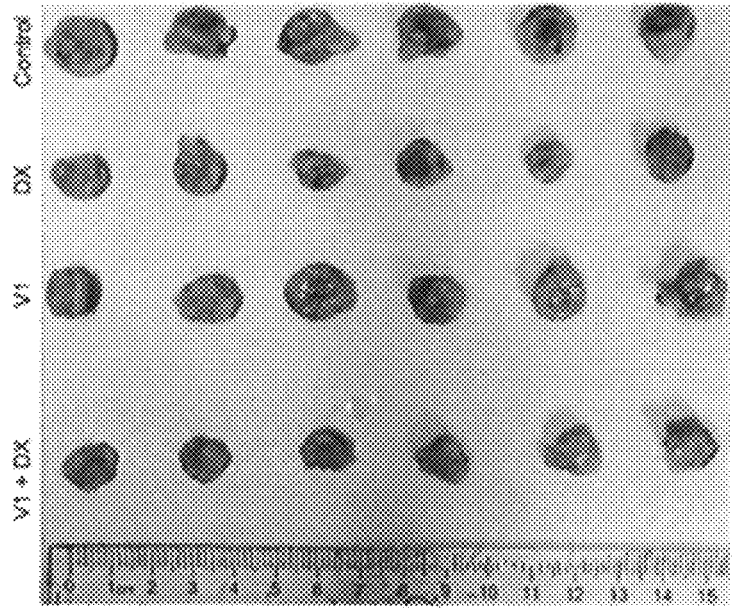
FIG. 11E is a series of optical images showing the size of dissected tumors of the mice with or without subjected to treatment.
Figure 11F:
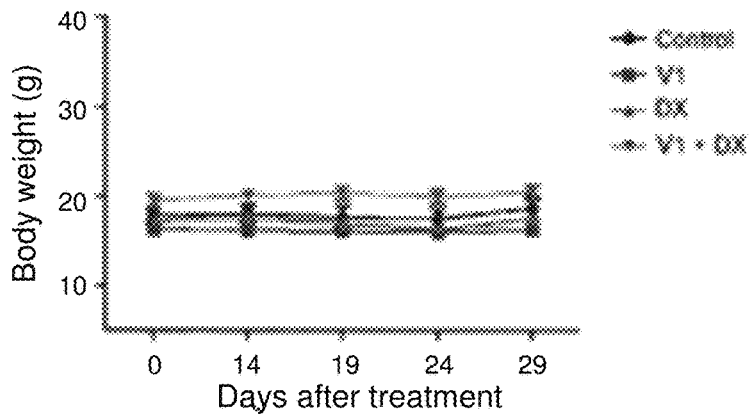
FIG. 11F is a line chart showing the body weight of the mice against days after treatment.

Anti-Metastasis Effect of V1 in Combination with Chemotherapeutic Drugs on Cancer Cells In some cases, for example, patients with advanced or metastatic breast cancer may require chemotherapy as an additional treatment. Thus, the inventors have further assessed the combinatorial effects of V1 with a chemotherapy drug, doxorubicin, on the metastasis of breast cancers in a spontaneous cancer mouse model, established by fat pad injection of 4T1 mouse breast cancer cells into nude mice. After tumors were palpable (~5 mm, around day 9), the mice were randomly divided into four groups (six mice per group) and treated with buffer, V1 (20 mg/kg, IP, daily), doxorubicin, or a combination of V1 and doxorubicin for four weeks (FIG. 11A). As shown in FIGS. 11B-11E, doxorubicin significantly inhibited both tumor growth and metastasis, whereas V1 has on effects on tumor growth, but exhibited a higher inhibitory effect on metastasis as compared to doxorubicin. Interestingly, V1 in combination with doxorubicin failed to further inhibit tumor growth as compared to doxorubicin alone, but did exhibit, at least, an additive effect on metastasis as compared to either V1 or doxorubicin alone (FIGS. 11B-11E). Notably, neither treatment regimens markedly affects the mouse weight (FIG. 11F). In summary, the aforementioned data indicate that 6-morpholino-1,3,5-triazine derivatives such as V1 represent a novel class of anti-metastatic therapeutics, and can be used in the combination therapy with other therapeutics against cancer.

Example 4

Figure 12A:
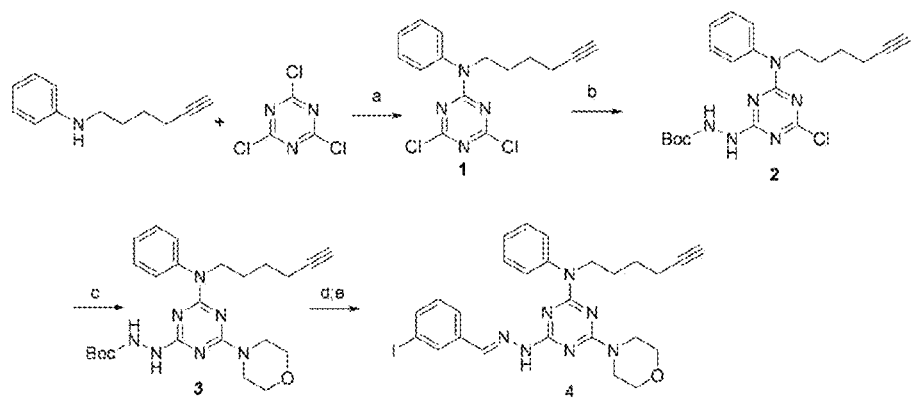
FIG. 12A is a synthetic scheme of a V1 analog carrying a clickable terminal alkynyl group.
Figure 12B:
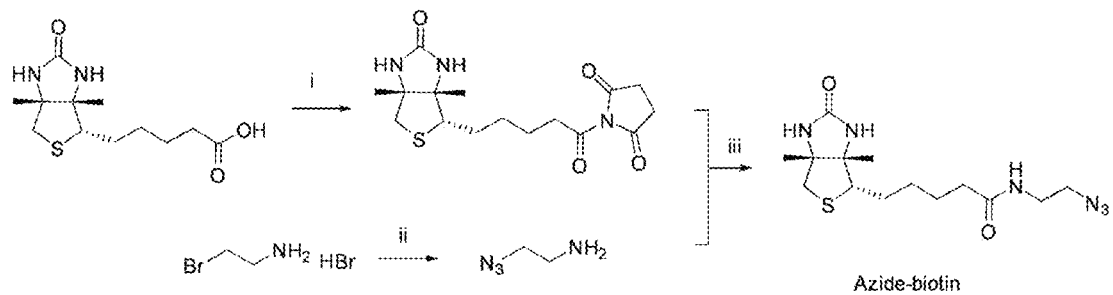
FIG. 12B is a synthetic scheme of azide-biotin.
Figure 12C:
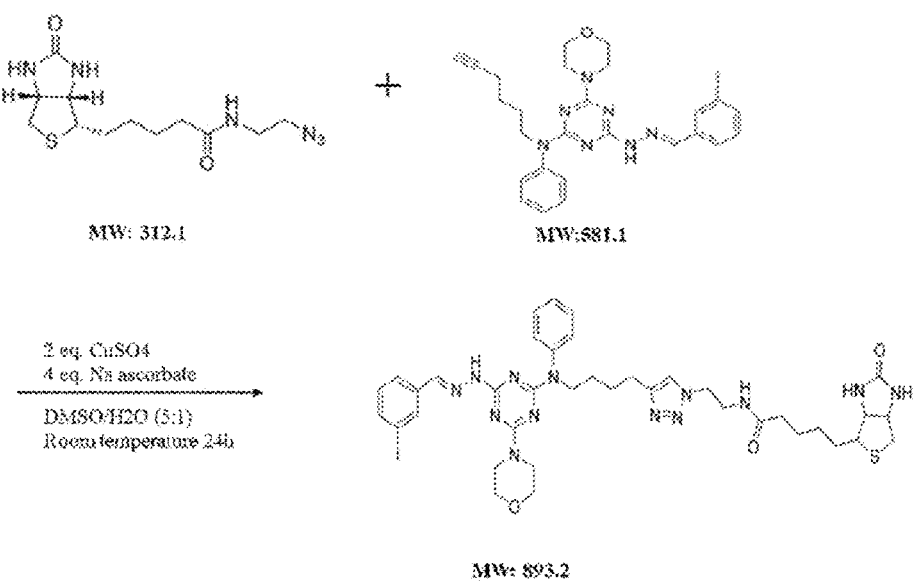
FIG. 12C is a synthetic scheme of Vi-biotin.
Figure 12D:
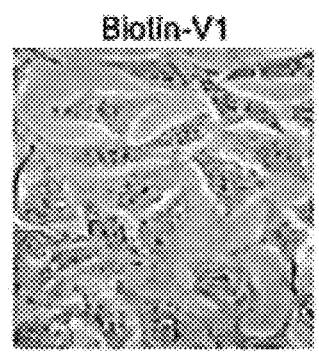
FIG. 12D is a microscopic image showing that Biotin-V1 induces large vacuoles in HeLa cells.
Figure 12E:
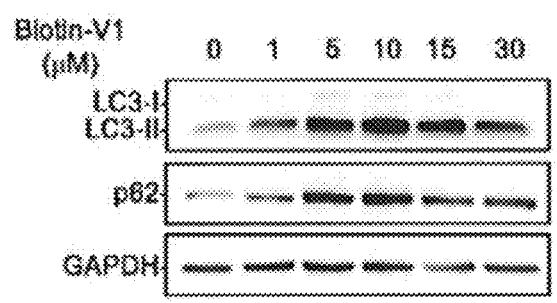
FIG. 12E is an immunoblot showing that Biotin-V1 induces accumulation of LC3-II and p62 in HeLa cells.
Figure 12F:
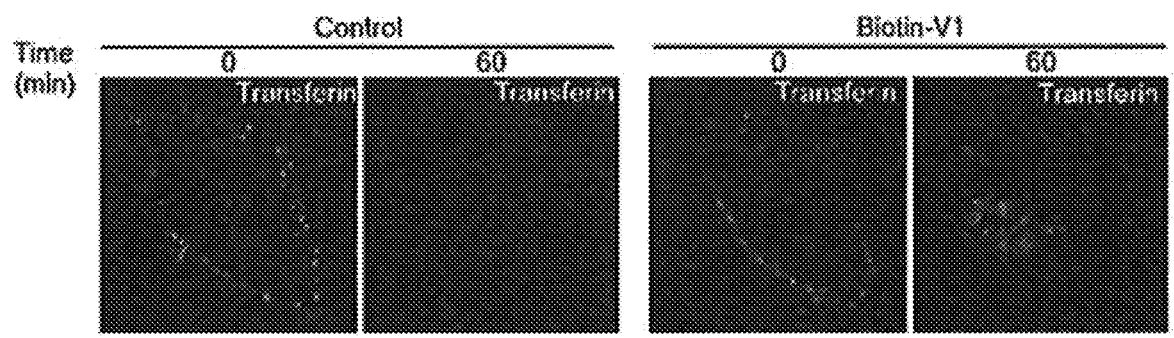
FIG. 12F is a series of microscopic images showing that Biotin-V1 inhibits transferrin degradation in HeLa cells.
Figure 13A:
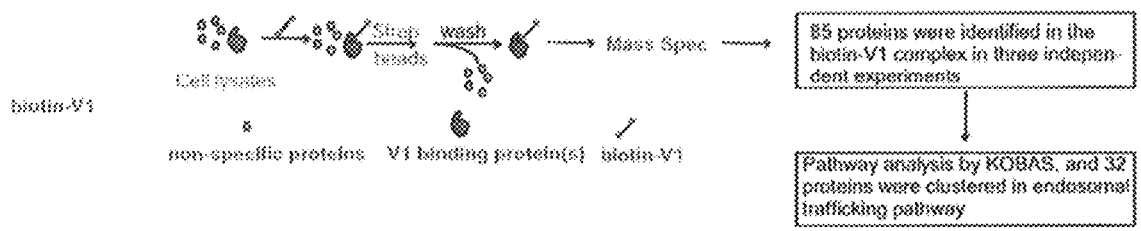
FIG. 13A is a schematic diagram illustrating the process flow of analyzing the binding protein of Vi-biotin.
Figure 13B:
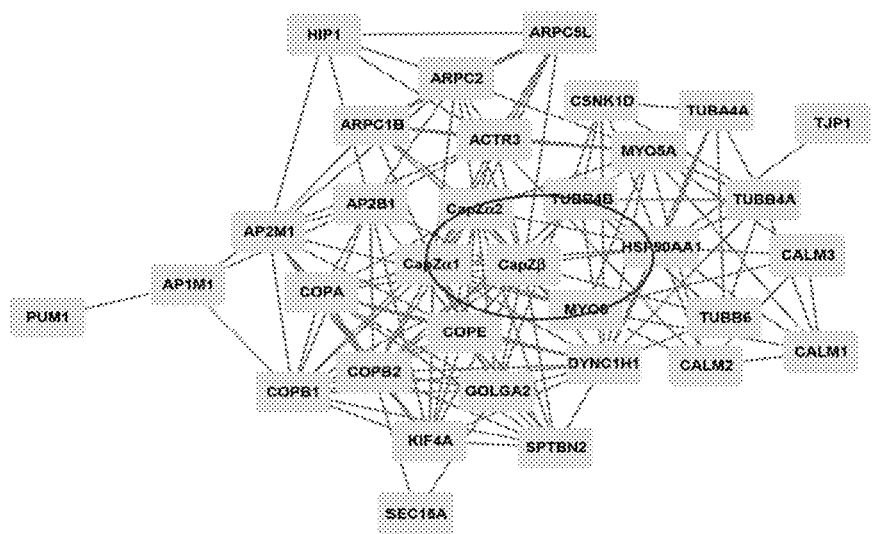
FIG. 13B is a schematic diagram illustrating a protein-protein interaction network based on the protein identified from the process of FIG. 13A using String software.
Figure 13C:
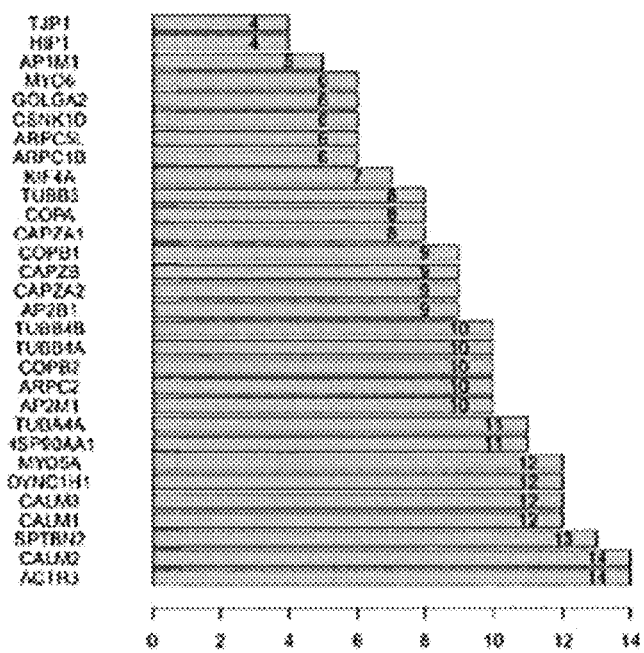
FIG. 13C is a bar chart showing the number of peptide of each of the proteins identified from the process of FIG. 13A.

V1 Targets Capping Protein Z (CapZ) to Inhibit Endosomal Trafficking and Metastasis To identify the V1 binding protein(s), the inventors have synthesized a V1 analogue, biotin-V1 (FIGS. 12A-12C), and found that biotin-V1 is a V1 agonist, manifested by its ability to induce vacuoles (FIG. 12D), induce LC3-II and p62 accumulation (FIG. 12E), and inhibit transferrin degradation (FIG. 12F). Subsequently, biotin-V1 was administered to HeLa cell extracts, the V1 binding complex was purified with streptavidin beads, and subjected to mass analysis. There were 85 potential V1 binding proteins identified in three independent experiments with high fidelity (FIG. 13A). Among them, 32 proteins were clustered in endocytosis and vesicle-mediated transport pathways using KOBAS online software. After construction of a protein-protein interaction network using these 32 proteins through String software, several hub proteins were exhibited, including GOLGA2, CapZα1, CapZβ, SPTBN2 and MYOSA (FIGS. 13B and 13C).

Figure 14A:
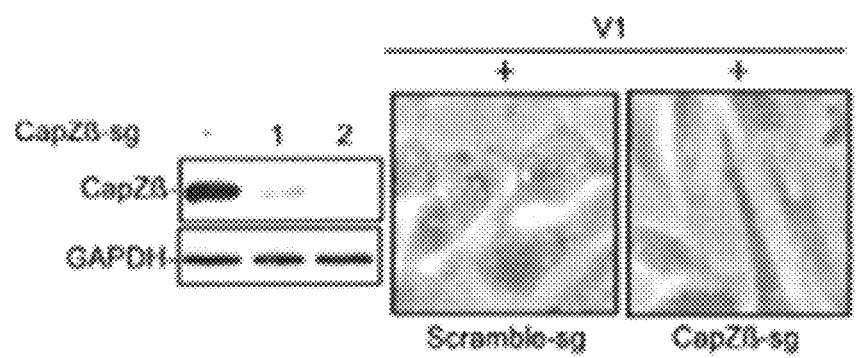
FIG. 14A is an immunoblot and a pair of microscopic images of HeLa cells with their Capβ being knocked out and the knockout abolished the ability of V1 to induce large vacuoles in the HeLa cells.
Figure 14B:
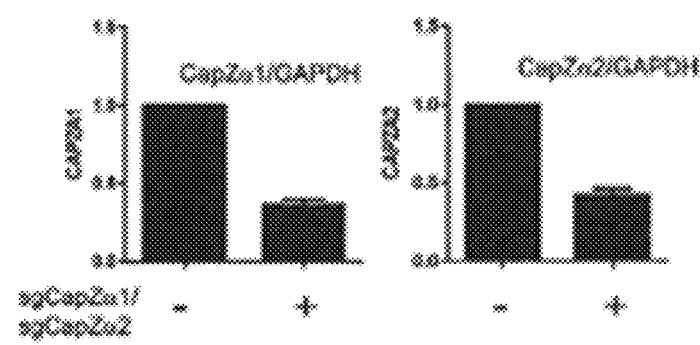
FIG. 14B is a pair of bar charts and microscopic images showing that the expression of CapZα1 and CapZα2 were knocked down by sgRNAs in HeLa cells and the double knockdown of CapZα1/2 abolished V1-induced large vacuoles in HeLa cells.
Figure 14B:
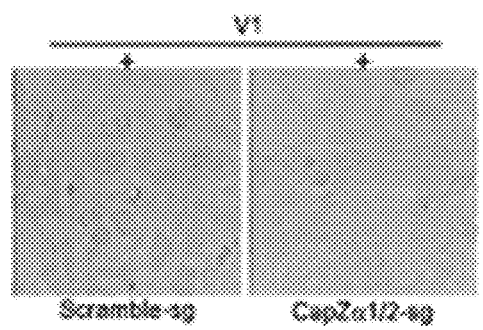
Figure 14C:
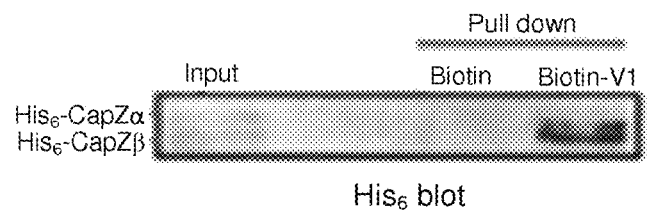
FIG. 14C is an immunoblot showing Biotin-V1 interacts with purified $His_6$-CapZα and $His_6$-CapZβ recombinant proteins.
Figure 14D:
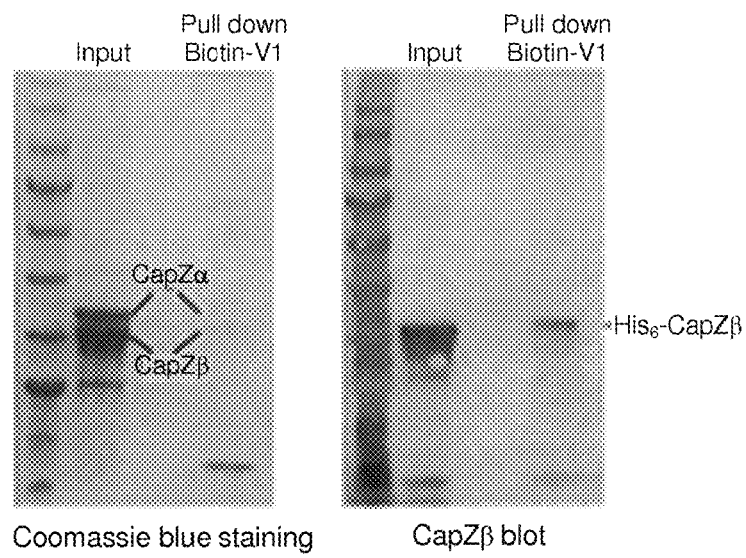
FIG. 14D is a pair of immunoblots of purified CapZα and CapZβ recombinant proteins after incubated with Biotin-V1.
Figure 14E:
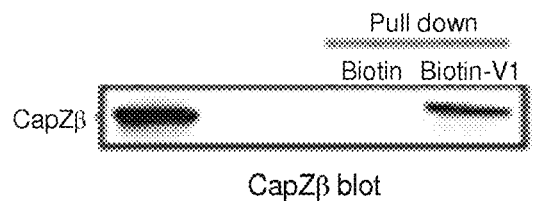
FIG. 14E is a CapZβ immunoblot of lysate of HeLa cells treated with biotin or Biotin-V1.

The expression of these genes in HeLa cells were knocked out by CRISPR/Cas9 to assess whether the ability of V1 inducing vacuole formation or endocytosis arrest would be affected by these knockdowns. Interestingly, only knockout of CapZβ or CapZα abolished the ability of V1 to induce vacuoles in HeLa cells (FIGS. 14A and 14B). CapZα and CapZβ are the α and β subunits of the actin capping protein (CP), also called CapZ, and the CapZβ-CapZα heterodimeric complex normally binds to the barbed ends of actin filaments to prevent further filament elongation. To investigate whether biotin-V1 or biotin alone would be able to bind with the CapZβ-CapZα heterodimeric complex, the inventors have incubated biotin or bioin-V1 with purified $His_6$-CapZα and $His_6$-CapZβ recombinant proteins, or purified CapZα and CapZβ proteins, followed by subjecting the mixture to streptavidin pulldown. The streptavidin pulldowns were analyzed by His6 immunoblotting, coomassie blue staining or CapZβ immunoblotting. As shown in FIGS. 14C and 14D, it is manifest that biotin-V1, not biotin alone, interacts with the recombinant CapZβ-CapZα heterodimer, preferably CapZβ, in vitro. In addition, in another experiment, HeLa cells were treated with biotin or biotin-V1 and the lysate thereof was incubated with streptavidin beads, followed by subjecting to streptavidin pulldown. The streptavidin pulldowns were analyzed by CapZβ immunoblotting and the results indicate that CapZβ was pulled down from the extract of HeLa cells treated with biotin-V1, but not biotin (FIG. 14E), suggesting that CapZ is V1's binding protein.

Figure 15A:
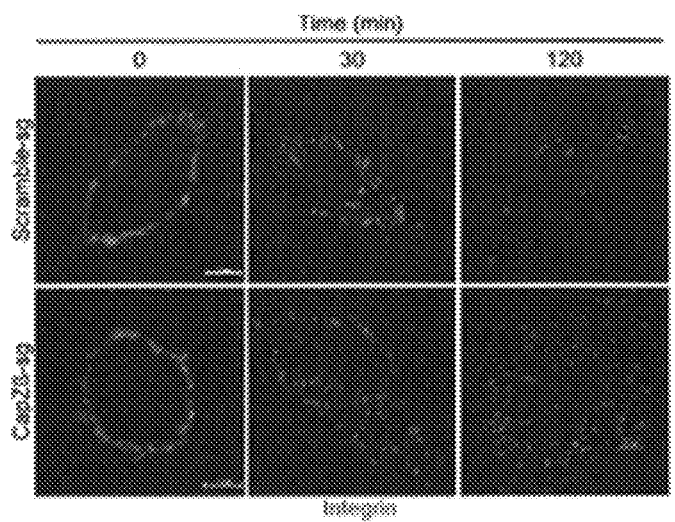
FIG. 15A is a series of microscopic images of HeLa cells with their Capβ being knocked out and the knockout inhibited integrin recycling in the HeLa cells.
Figure 15B:
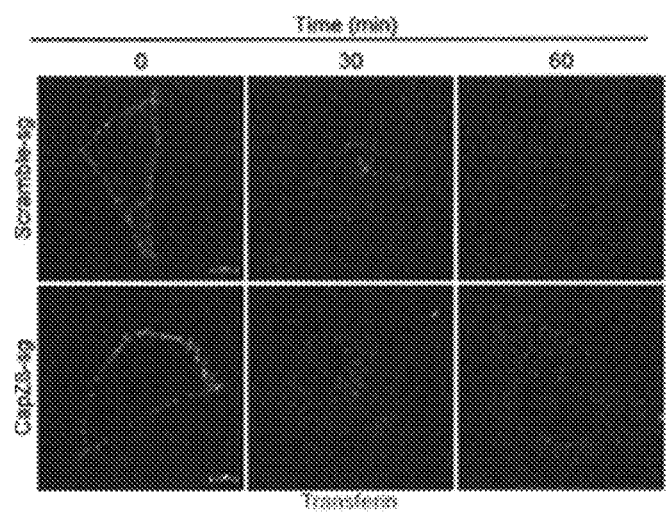
FIG. 15B is a series of microscopic images of HeLa cells with their Capβ being knocked out and the knockout inhibited transferrin degradation in the HeLa cells.
Figure 15C:
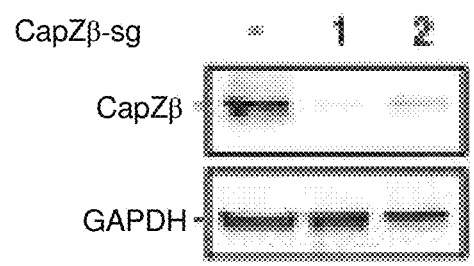
FIG. 15C is an immunoblot of 4T1 cells with their CapZβ being knocked out by sgRNA.
Figure 15D:
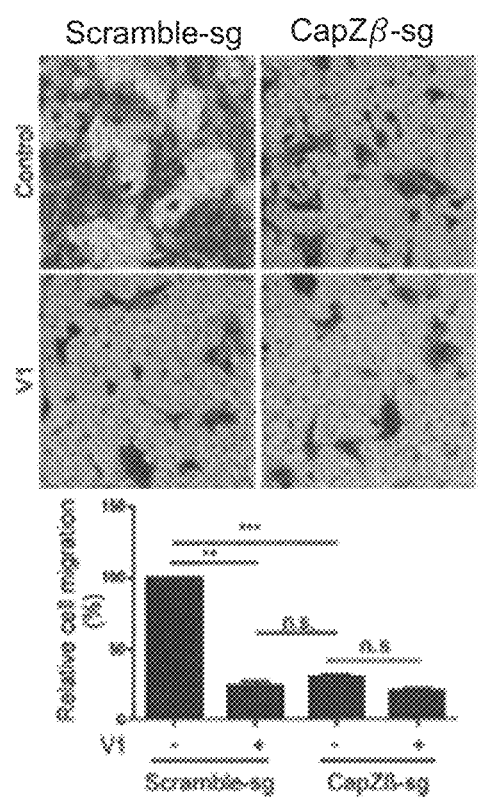
FIG. 15D is a series of microscopic images and a bar chart showing the knockout of CapZβ inhibited migration of 4T1 cells and V1 treatment exhibited no further inhibition on such migration.

The role of CapZ in endosomal trafficking was examined, and it is found that CapZ knockout abolished integrin recycling (FIG. 15A) and transferrin degradation (FIG. 15B) in HeLa cells. The role of CapZ in the migration of cells treated with or without V1 was examined as well. As shown in FIGS. 15C and 15D, CapZ knockout markedly inhibited the migration of 4T1 cells and treatment of the CapZ-knockout cells with V1 has no additional inhibitory effect on cell migration. These data suggest that CapZ is an effector of V1 in endosomal trafficking and migration. The role of CapZ in metastasis was further studied using a spontaneous cancer mouse model with fat pad injection of control or CapZ-knockout 4T1 breast cancer cells into female nude mice. The lungs of each group of mice were collected after one month and stained with ink. The tumor nodules in the lungs were quantified and the tumor size was measured every 5 days during the experiment.

Figure 16A:
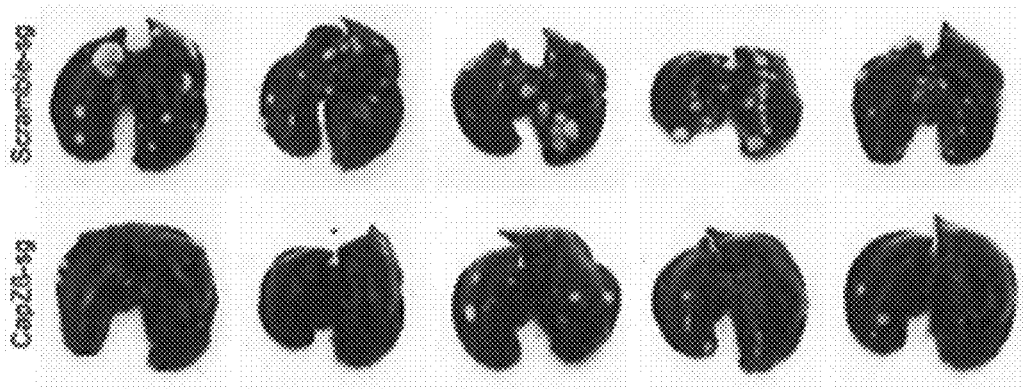
FIG. 16A is a series of optical images showing the excised lungs of female nude mice with their fat pad being injected with 4T1 cells or CapZβ-knockout 4T1 cells.
Figure 16B:
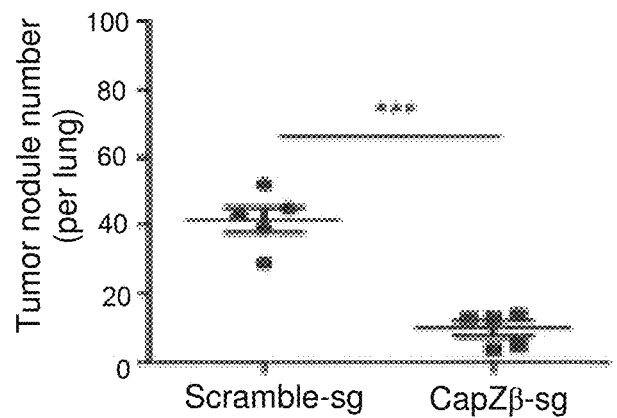
FIG. 16B is a line plot showing the number of tumor nodules of the excised lungs of FIG. 16A.
Figure 16C:
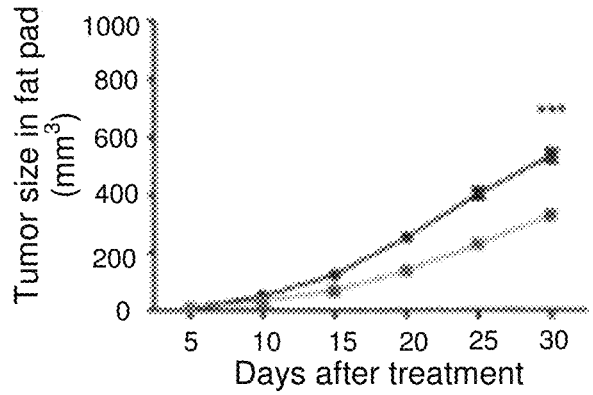
FIG. 16C is a line chart showing the tumor size in fat pat of the female nude mice of FIG. 16A against days after treatment.

As shown in FIGS. 16A and 16B, knocking out CapZ significantly inhibited the metastasis of 4T1 cells, manifested by a fewer number of tumor nodules per lungs in mice implanted with CapZ-knockout cells as compared to the mice implanted with the control cells, indicating that CapZ is involved in tumor metastasis in viva. Notably, the tumor growth in mice implanted with CapZ-knockout 4T1 cells was slower than the mice implanted with the control cells (FIG. 16C), it is likely attributed to the canonical role of CapZ in regulating actin polymerization. Nevertheless, these results suggest that CapZ is the effector mediating the ability of V1 to inhibit endocytosis, migration and metastasis.

Example 5

CapZ Regulates Earlier Endosome Maturation

Figure 17A:
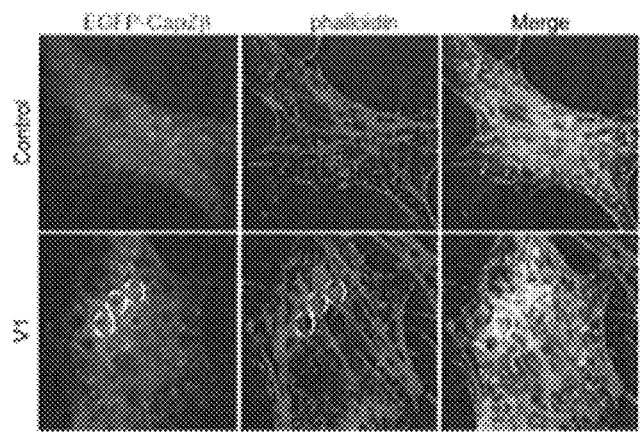
FIG. 17A is a series of microscopic images showing Capβ-GFP-expressing HeLa cells treated with or without V1 (1 μM) immunostained with rhodamine phalloidin. The dot circles indicate the V1-induced vesicular structures.
Figure 17B:
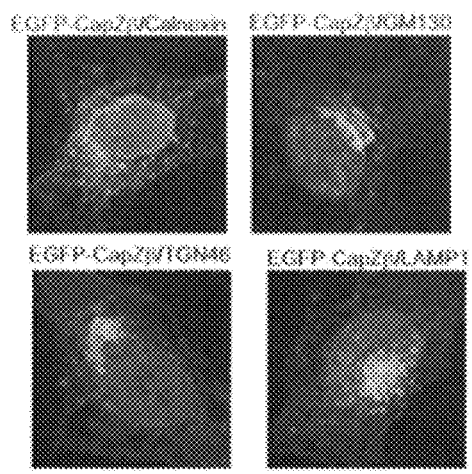
FIG. 17B is a series of microscopic images showing Capβ-GFP-expressing HeLa cells treated with or without V1 (1 μM) immunostained with Calnexin, GM130, TGN46, or LAMP1 antibody.
Figure 17C:
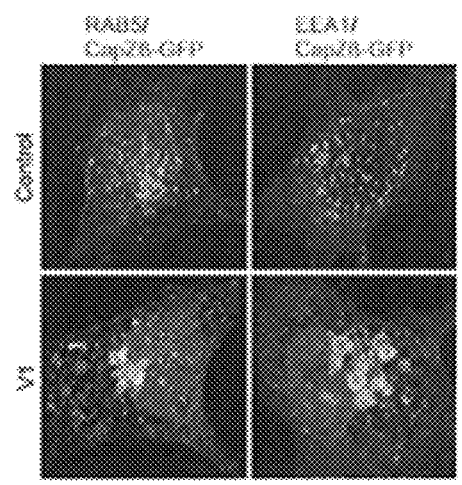
FIG. 17C is a series of microscopic images showing Capβ-GFP-expressing HeLa cells treated with or without V1 (1 μM) immunostained with RAB5 or EEA1 antibody.
Figure 17D:
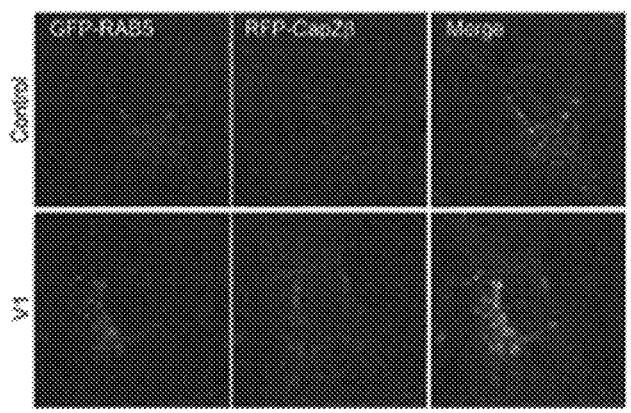
FIG. 17D is a series of microscopic images showing RFP-CapZβ and GFP-RAB5A-expressing HeLa cells treated with or without V1 (1 μM).
Figure 17E:
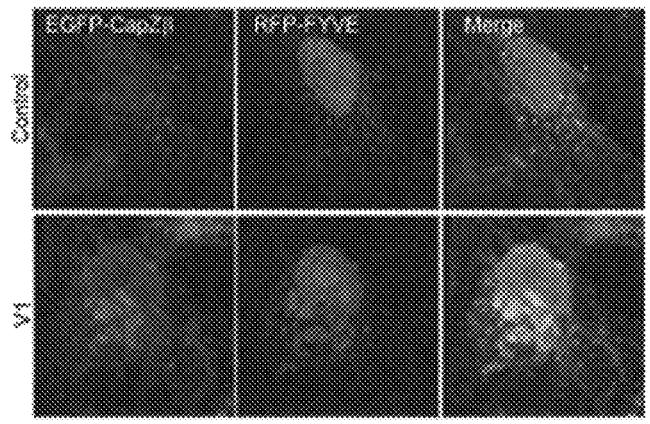
FIG. 17E is a series of microscopic images showing EGFP-CapZβ and RFP-FYVE-expressing HeLa cells treated with or without V1 (1 μM).
Figure 17F:
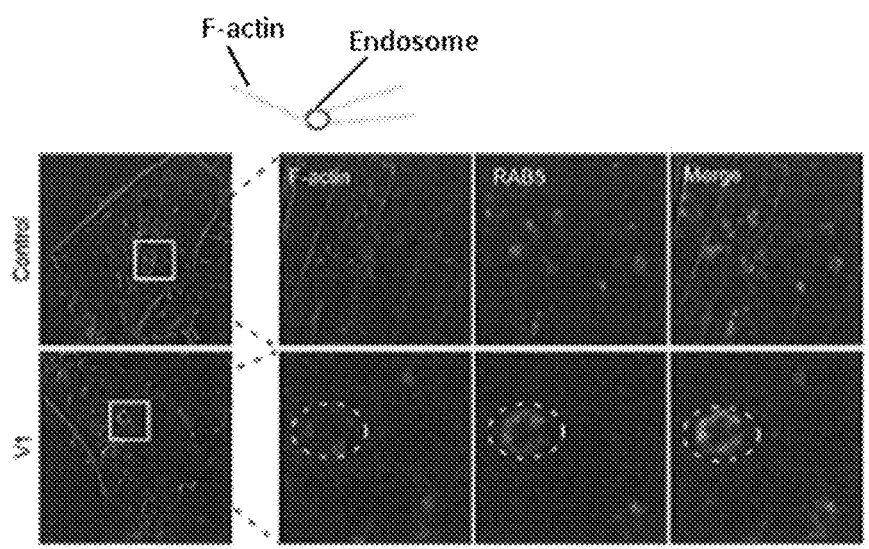
FIG. 17F is a series of microscopic images showing HeLa cells treated with or without V1 (1 μM) co-immunostained with RAB5 antibody and rhodamine phalloidin.
Figure 17G:
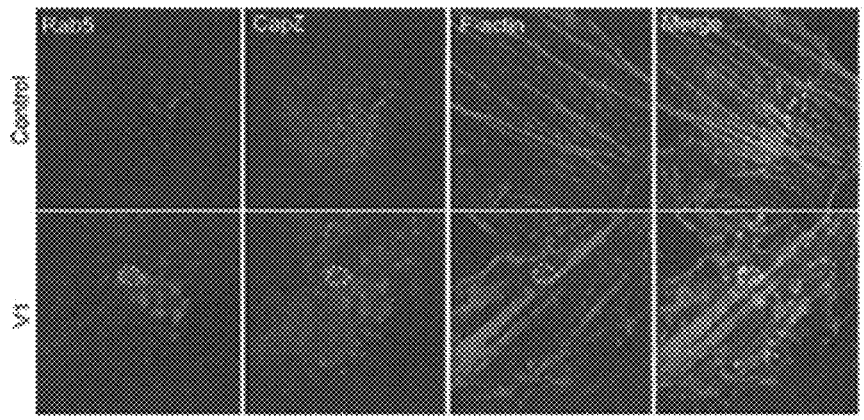
FIG. 17G is series of microscopic images showing HeLa cells treated with or without V1 (1 μM) co-immunostained with RAB5 antibody, CapZ, and rhodamine phalloidin. The dot circles indicate the tight association of RAB5, CapZ and rhodamine phalloidin.

To further study the role of CapZ in endocytosis, the subcellular localization of CapZ was examined by immunofluorescence staining. As shown in FIG. 17A, both diffused and puncta CapZ were detected in CapZβ-GFP-expressing HeLa cells, and majority of the CapZ puncta were co-localized with the F-actin puncta (phalloidin staining), confirming that CapZ is localized at the tips of actin filaments. In V1-treated cells, some CapZ puncta were apparently organized into large vesicular structures. To determine the identity of these CapZ positive vesicular structures in the V1-treated cells, the inventors have examined whether the CapZ puncta are localized at any known cellular organelles. On one hand, the CapZ puncta exhibited weak co-localization with Calnexin (an ER protein), GMI30 (a cis-Golgi protein), TGN46 (a trans-Golgi protein), or LAMP1 (a lysosomal protein) (FIG. 17B). On the other hand, these CapZ puncta were strongly associated with the early endosome markers, EEA1, RAB5, or PI3P; and in V1-treated cells, some of these CapZ puncta were strikingly accumulated at the surface of the enlarged endosomes (FIGS. 17C-17E). Likewise, the RAB5-positive early endosomes were co-localized with the F-actin puncta (phalloidin staining), and the F-actin puncta were also accumulated at the surface of V1-induced enlarged early endosomes (FIGS. 17F and 17G). These data suggest that early endosomes are attached to the ends of actin filaments, likely via CapZ.

Figure 18A:
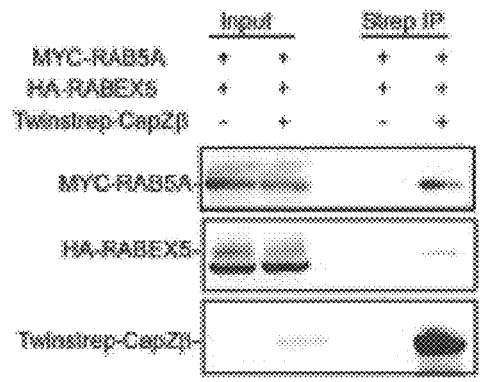
FIG. 18A is an immunoblot of lysate of HeLa cells transiently transfected with MYC-RAB5, HA-RABX5, and/or Twinstrep-CapZβ against CapZβ, RABEX5, and RAB5.
Figure 18B:
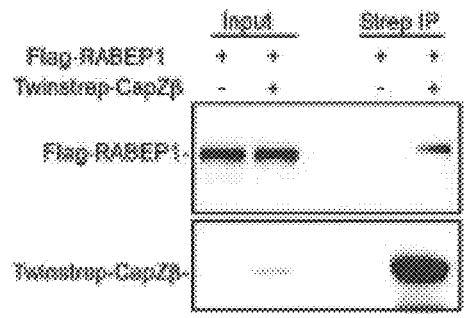
FIG. 18B is an immunoblot of lysate of HeLa cells transiently transfected with Flag-RABEP1 and/or Twinstrep-CapZβ against CapZβ or RABEP1.
Figure 18C:
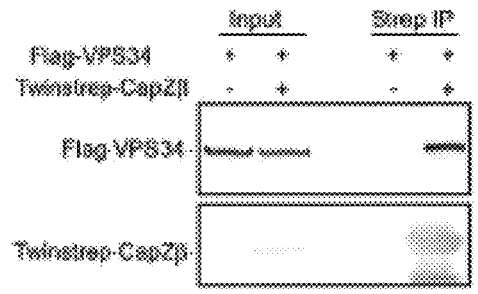
FIG. 18C is an immunoblot of lysate of HeLa cells transiently transfected with Flag-VPS34 and/or Twinstrep-CapZβ against CapZβ or VPS34.
Figure 18D:
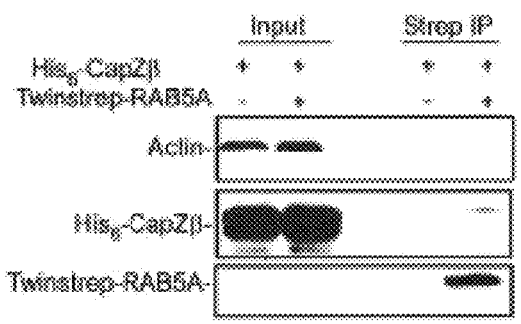
FIG. 18D is an immunoblot of lysate of HeLa cells transiently transfected with His6-CapZβ and/or Twinstrep-RAB5 against CapZβ, RAB5, and actin.
Figure 18E:
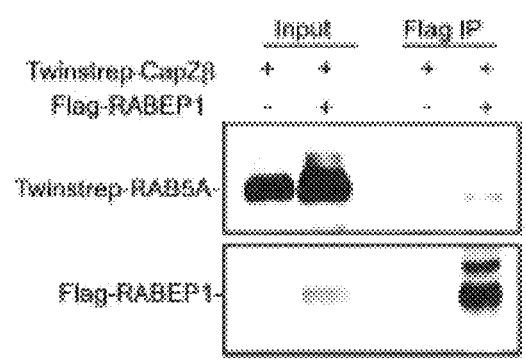
FIG. 18E is an immunoblot of lysate of HeLa cells transiently transfected with Twinstrep-CapZβ and Flag-RABEP1 against CapZβ or RABEP1.
Figure 18F:
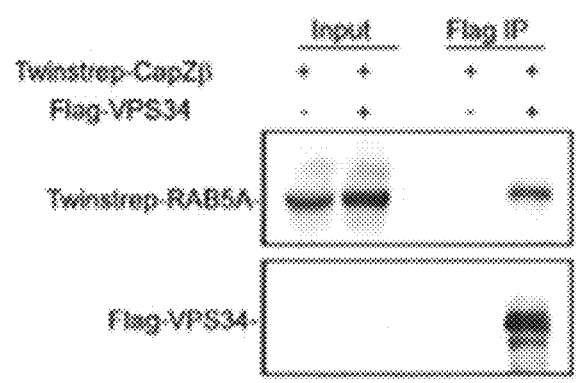
FIG. 18F is an immunoblot of lysate of HeLa cells transiently transfected with Twinstrep-CapZβ and Flag-VPS34 against CapZβ or VPS34.

To confirm the association of early endosomes with F-actin, co-immunoprecipitation experiments were performed to assess whether CapZ interacts with RAB5 or its effectors. As shown in FIGS. 18A-18C, in twinstrep-CapZβ expressing cells, streptavidin beads not only pulled down CapZβ, but also brought down RAB5A, and its effectors, e.g. RABEX5, RABEP1, and VPS34. Interestingly, CapZ, not actin, was found in the RAB5A or RABEP1 immunocomplex (FIG. 18D). Likewise, CapZβ was also found at the RABEP1 or VPS34 immunocomplexes (FIGS. 18E and 18F). These data may imply that CapZ is a bridging protein between the early endosomes and the actin filaments.

Figure 19:
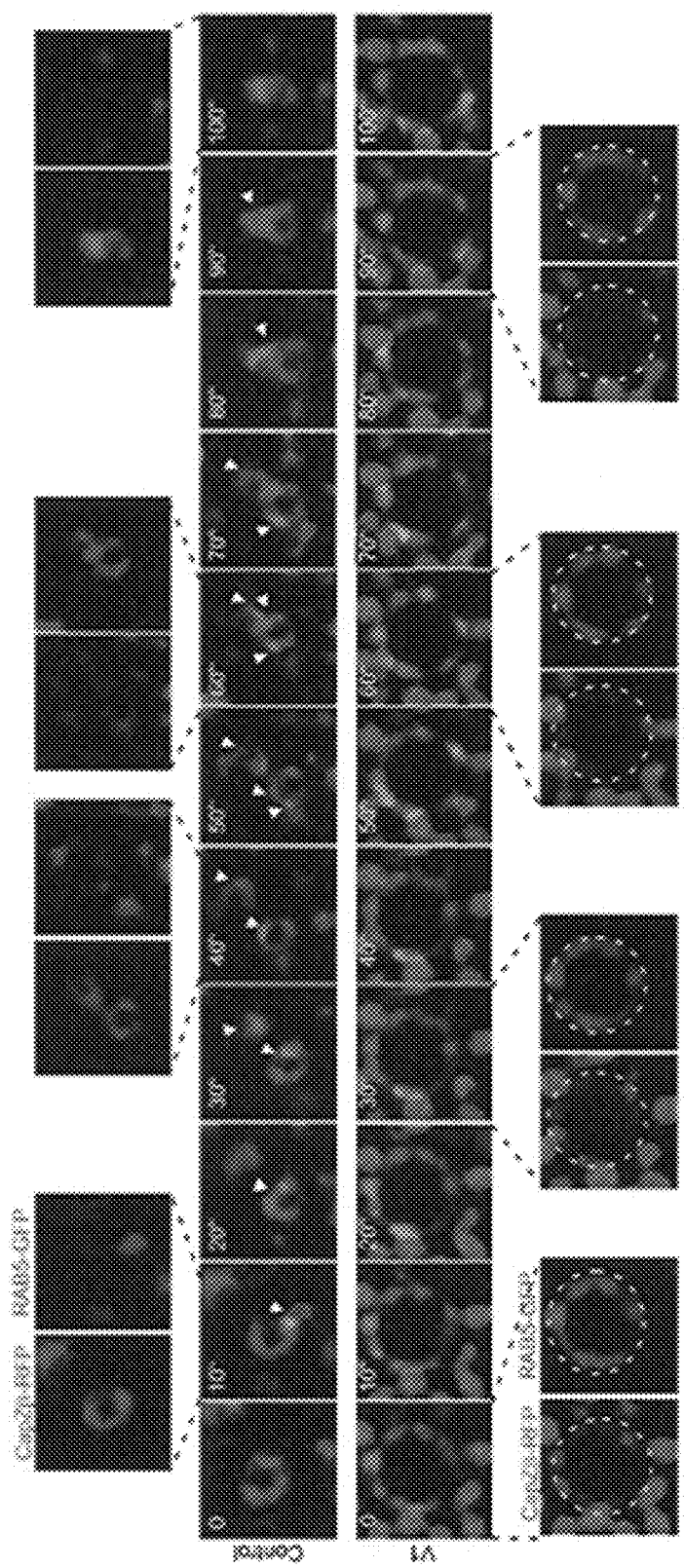
FIG. 19 is a series of time lapsed microscopic images of RAB5-GFP/CapZβ-RFP-expressing HeLa cells treated with or without V1 (1 μM). The arrows indicate the transient association of CapZ puncta with RAB5-positive endosome in control cells, and the dotted circles indicate the V1-induced tight association between CapZ and the enlarged RAB5-positive endosomes.

The temporal association of CapZβ with endosomes in RAB5-GFP/CapZβ-RFP expressing HeLa cells treated with or without V1 was further examined by live-cell fluorescence imaging in an N-SIM Super-Resolution Microscope system. In the control cells (i.e. without V1 treatment), the association of CapZβ to earlier endosomes was dynamic: CapZβ was first recruited to the RAB5-positive early endosomes, then two earlier endosomes were fused together, followed by the release of CapZ from the fused endosomes (top panel of FIG. 19). However, in V1-treated cells, the association of CapZβ with the earlier endosomes was static: CapZβ was locked with the enlarged RAB5-positive endosomes (bottom panel of FIG. 19). These results further suggest that the temporal association of CapZ with the early endosomes might play a dicliotomic role in controlling endosomal trafficking, in which its association with the endosomes is required for early endosome maturation, whereas its release from the endosomes is required for the transition of early endosome to late endosome.

Figure 20A:
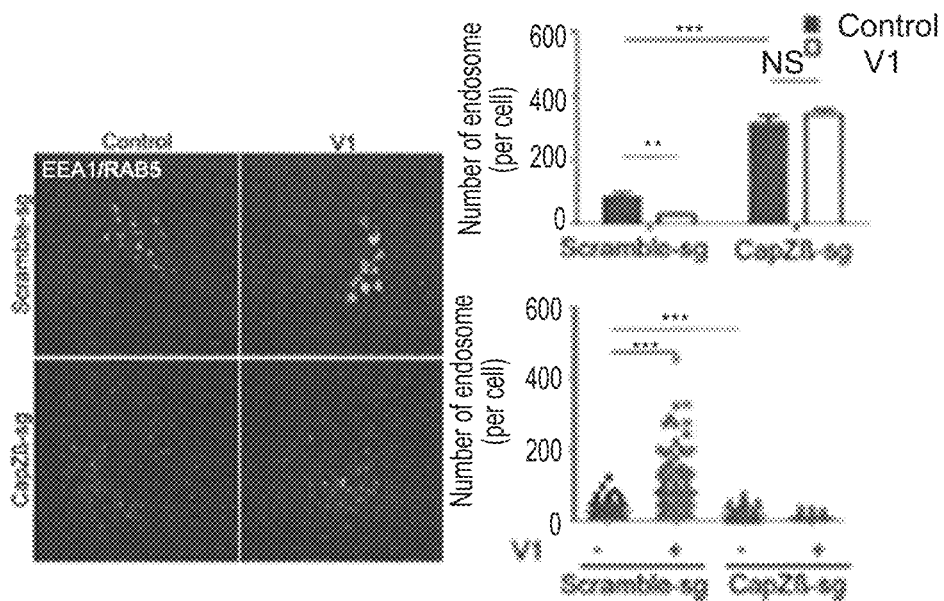
FIG. 20A is a series of microscopic images, a bar chart, and a line plot. The microscopic images show the control or CapZ-knockout HeLa cells treated with or without V1 (1 μM) immunostained with EEA1 or RAB5 antibody. The bar chart and the line plot respectively show the number and the size of earlier endosomes of the control or CapZ-knockout HeLa cells treated with or without V1.
Figure 20B:
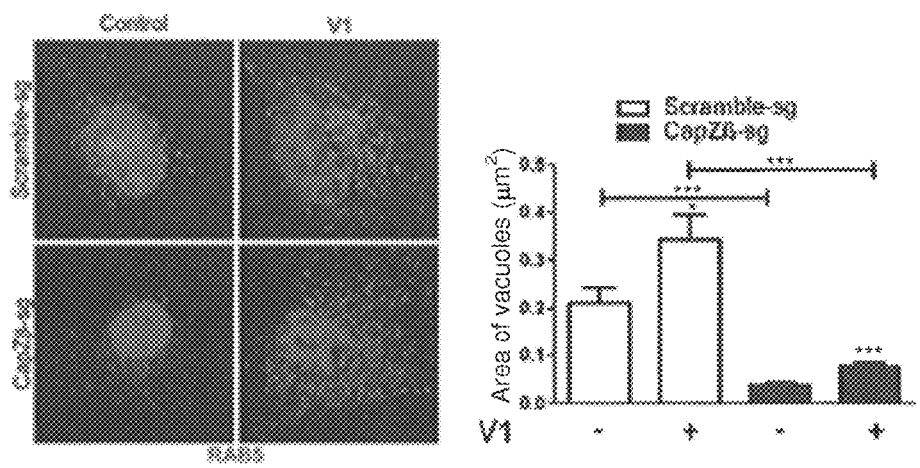
FIG. 20B is a series of microscopic images and a bar chart. The microscopic images show the control or CapZ-knockout HeLa cells treated with or without V1 (1 μM). The bar chat shows the number of earlier endosomes of the control or CapZ-knockout HeLa cells treated with or without V1.
Figure 20C:
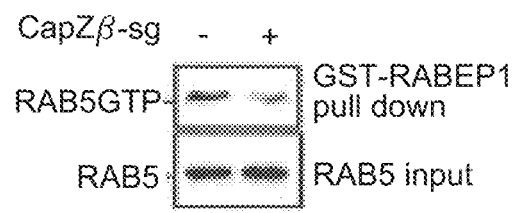
FIG. 20C is an immunoblot showing active RAB5 in control or CapZ knockout HeLa cells.

The size and the number of endosomes in CapZ-knockout HeLa cells were compared with the control cells so as to examine whether the association of CapZ with endosome is required for the maturation of earlier endosomes. It is manifest that the size of early endosomes in the CapZβ-knockout cells was much smaller than those in the control cells treated with or without V1, while the number of endosomes in CapZβ-knockout cells was significantly increased as compared with the control cells (FIGS. 20A and 20B). These results suggest that fusion of small early endosomes is blocked or inhibited in the CapZβ-knockout cells. Consistently, the level of RAB5-GTP in the CapZβ-knockout cells was significantly lower than that in the control cells (FIG. 20C), indicating that RAB5 is less active in CapZβ-knockout cells.

Figure 21A:
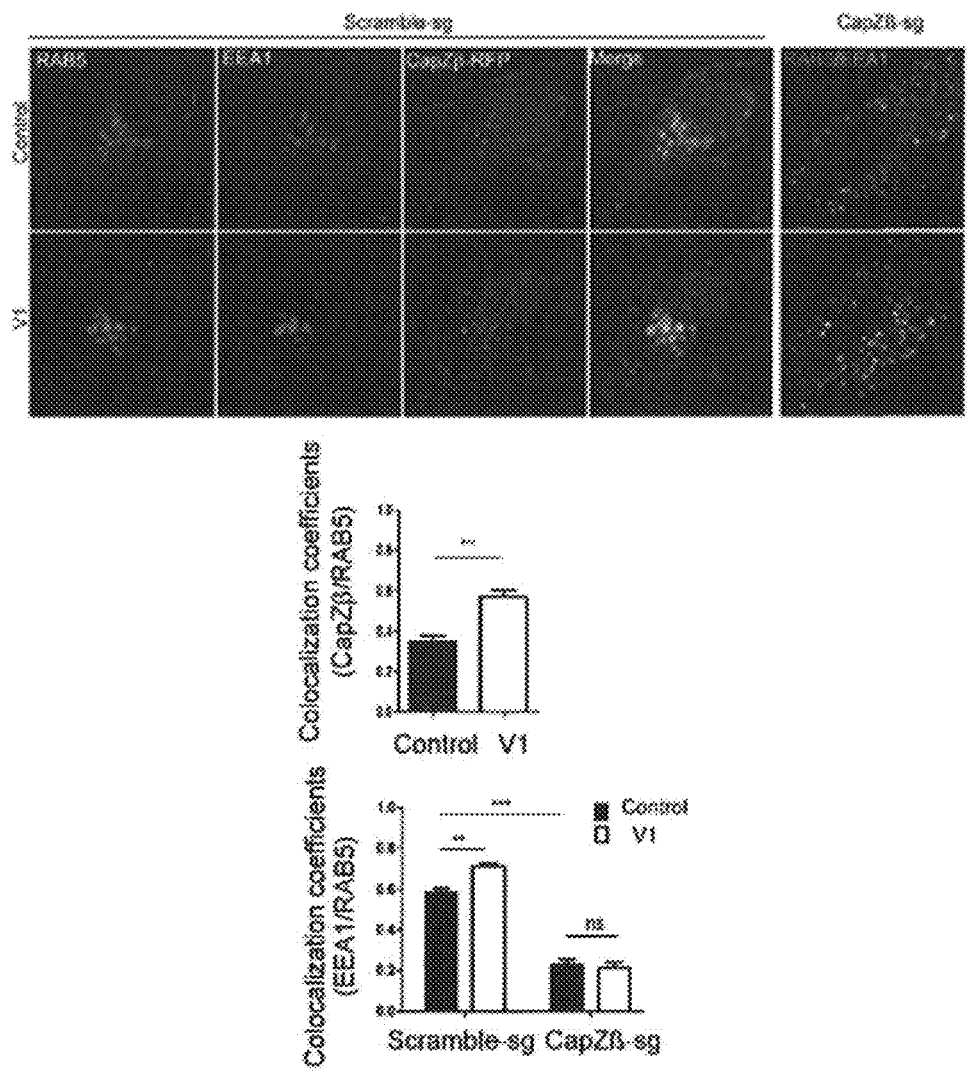
FIG. 21A is a series of microscopic images and bar charts. The microscopic images show the CapZβ-RFP-expressing or CapZ-knockout HeLa cells treated with or without V1 (1 μM), and immunostained with EEA1 or RAB5 antibody. The bar charts respectively show the co-localization coefficients of CapZ/RAB5 and EEA1/RAB5.
Figure 21B:
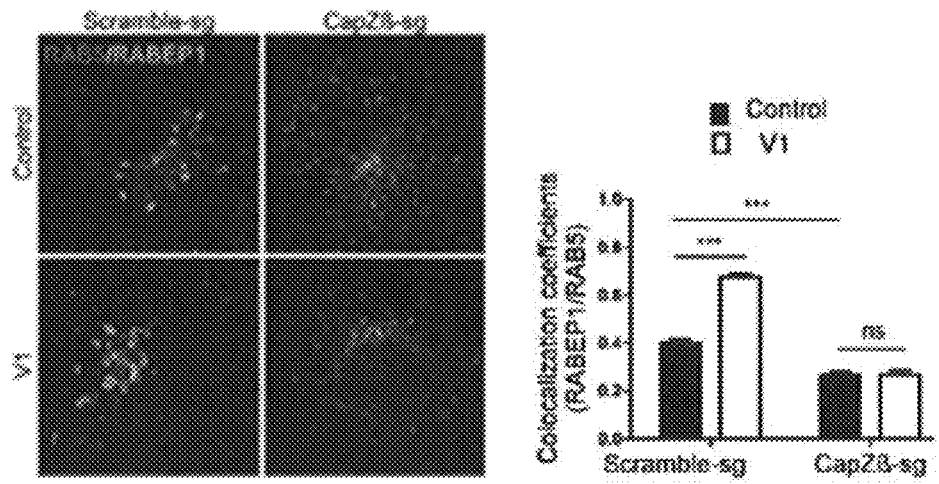
FIG. 21B is a series of microscopic images and a bar chart. The microscopic images show the control or CapZ-knockout HeLa cells treated with or without V1 (1 μM), and immunostained with RAB5 or RABEP1 antibody. The bar chart shows the co-localization coefficients of RABEP1/RAB5.
Figure 21C:
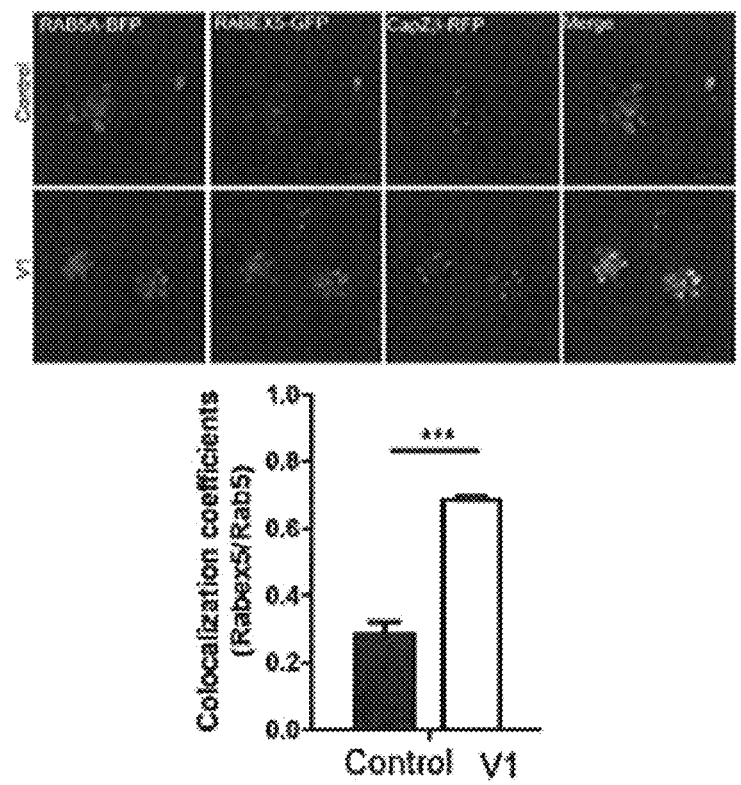
FIG. 21C is a series of microscopic images and a bar chart. The microscopic images show the CapZβ-RFP-expressing or CapZ-knockout HeLa cells transiently transfected with RAB5A-BFP, RABEX5-GFP, and CapZβ-REF, and treated with or without V1 (1 μM). The bar chart shows the co-localization coefficients of RABEX5/RAB5.
Figure 21D:
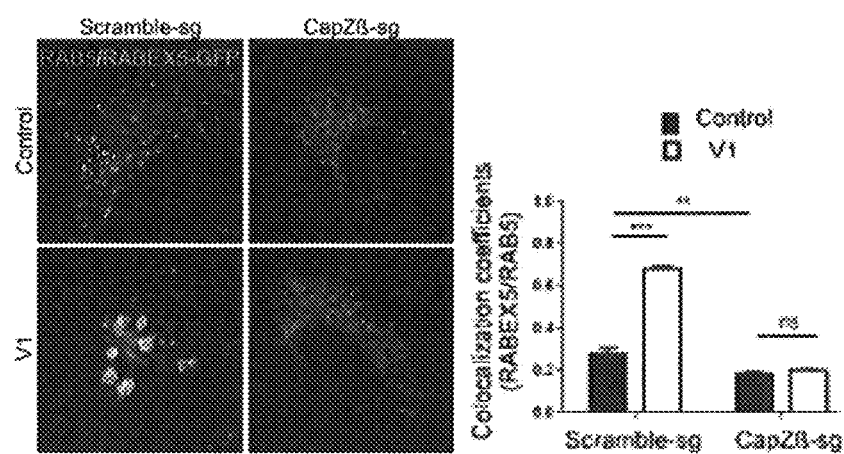
FIG. 21D is a series of microscopic images and a bar chart. The microscopic images show the control or CapZ-knockout HeLa cells transiently transfected with RABEX5-GFP, and treated with or without V1 (1 μM).
Figure 21E:
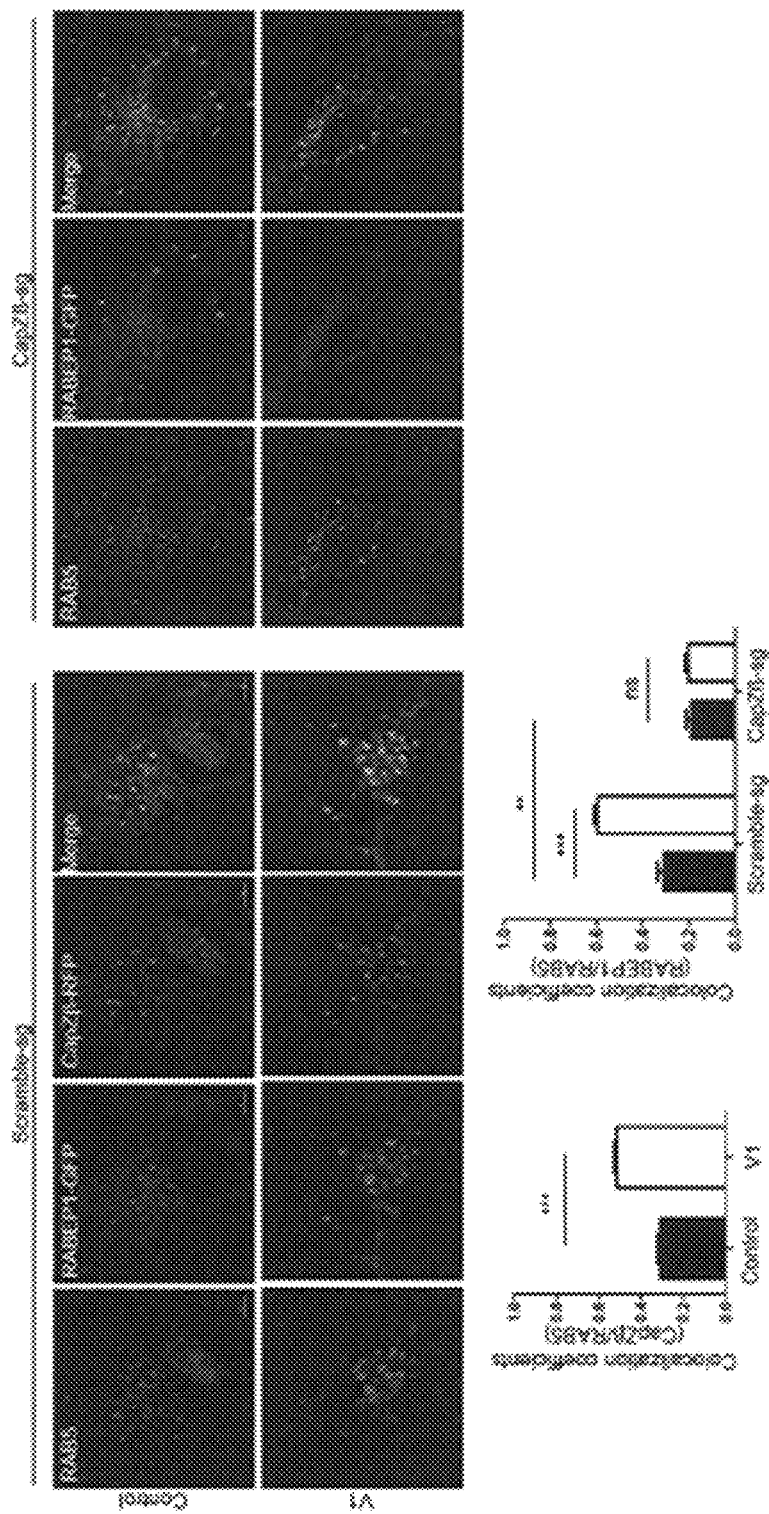
FIG. 21E is a series of microscopic images and bar charts. The microscopic images show the CapZβ-RFP-expressing or CapZ-knockout HeLa cells transiently transfected with RABEP1-GFP, and treated with or without V1 (1 μM), followed by being immunostained with RAB5. The bar charts respectively show the co-localization coefficients of RABEP1/RAB5 and CapZ/RAB5.
Figure 21F:
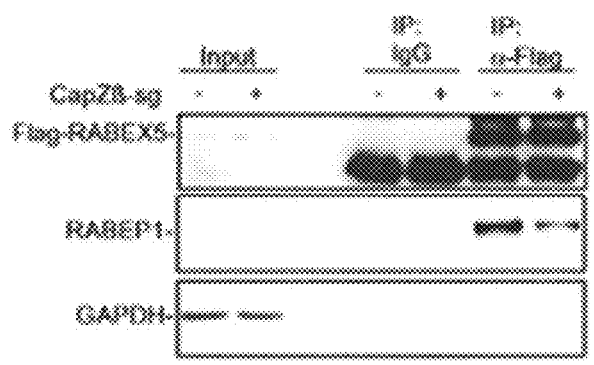
FIG. 21F is an immunoblot showing the lysate of control or CapZ-knockout HeLa cells transiently transfected with Flag-RABEX5 against RABEX5 and RABEP1.
Figure 21G:
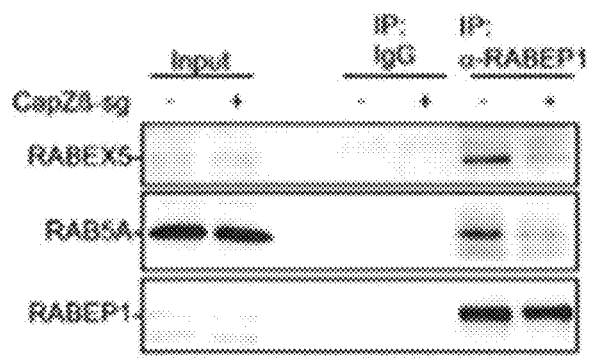
FIG. 21G is an immunoblot showing the lysate of control or CapZ-knockout HeLa cells against RABEX5, RABEP1, and RAB5.

The effects of CapZ knockout on the association of RAB5 with its effectors during endocytosis were further examined by immunofluorescence staining. As expected, V1 treatment significantly induced the co-localization between RAB5 with its effectors, e.g. EEA1 (FIG. 21A), RABEP1 (FIGS. 21B and 21C), and RABEX5 (FIG. 21D). In contrast, CapZβ knockout abolished the V1-induced RAB5 co-localization with EEA1 (FIG. 21A), or RABEP1 (FIG. 21B), and RABEX5 (FIG. 21D). Notably, CapZ knockout also significantly inhibited the association of RAB5 with RABEP1 (FIG. 21B) and RABEX5 (FIG. 21D) even in the absence of V1 treatment. Since the recruitment of the complex of RABEP1 and RABEX5 (an RAB5 GEF) to early endosome by endosomal RAB5 is required to maintain the RAB5-GTP level, these results suggest that CapZ might help RAB5 activation via RABEP1 or/and RABEX5. Thus, the role of CapZ in the formation of RABEPI-RABEX5 complex was investigated by co-immunoprecipitation experiments. Consistently, CapZβ knockout markedly decreased the interaction between RABEP1 with RABEX5 or RAB5 (FIGS. 21F and 21G). Taken together, these results suggest that CapZ helps the recruitment of RABEX5 and RABEP1 to endosome to activate RAB5 during early endosome maturation.

Figure 22A:
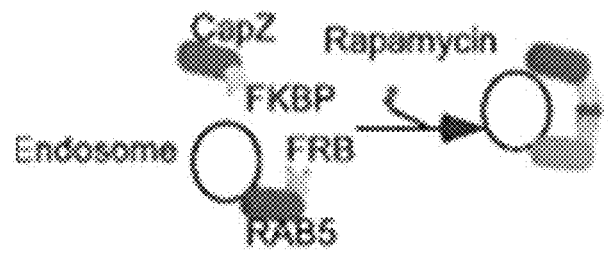
FIG. 22A is a schematic diagram illustrating the strategy to induce a stable association of CapZ with endosomes by conjugating RAB5 with FRB and CapZβ with FKBP in the presence of rapamycin.
Figure 22B:
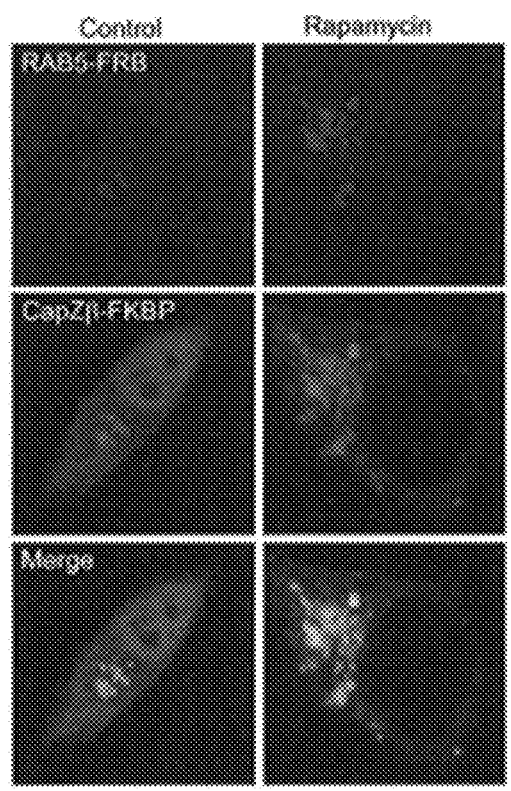
FIG. 22B is a series of microscopic images showing HeLa cells transiently transfected with FRB-RAB5 and FKBP-CapZβ, and incubated with rapamycin for 12 h to induce the interaction between RAB5 and CapZβ.
Figure 22C:
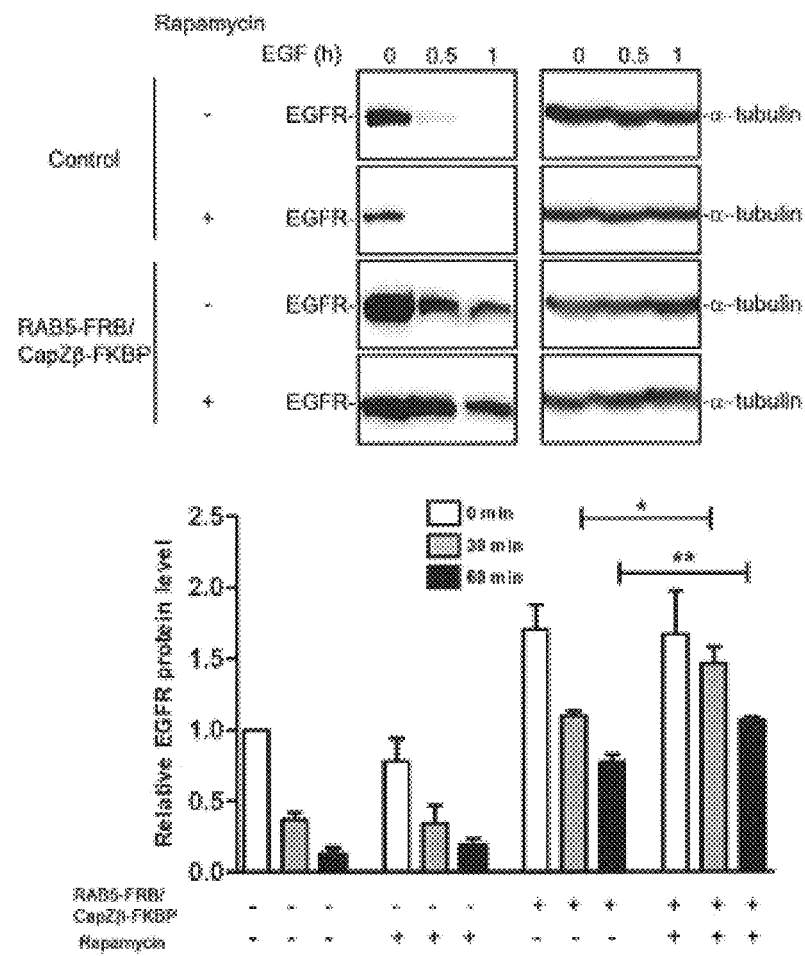
FIG. 22C is a series of immunoblots and a bar chart showing the level of EGFR of the control or FRB-RAB5/FKBP-CapZβ-expressing HeLa cells incubated with or without rapamycin for 12 h, and treated with EGF for the indicated time.
Figure 22D:
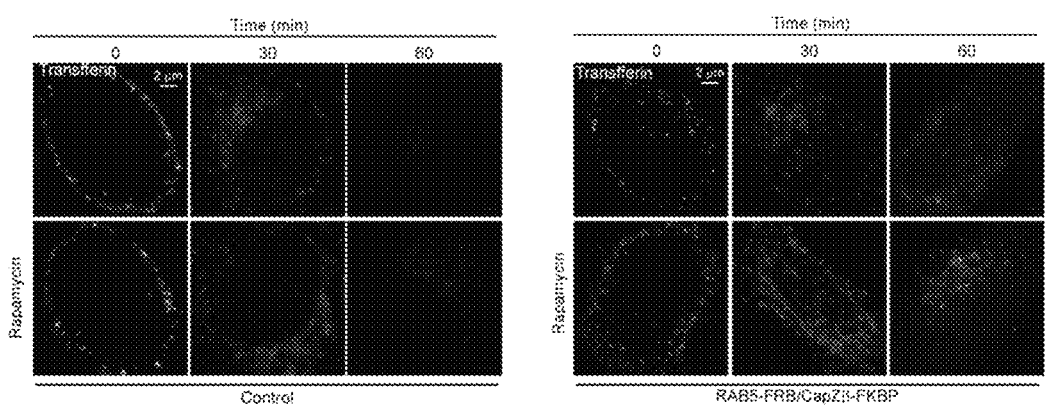
FIG. 22D is a series of microscopic images showing the results of immunofluorescence analysis of transferrin degradation in control or FRB-RAB5/FKBP-CapZβ-expressing HeLa cells incubated with or without rapamycin.
Figure 22E:
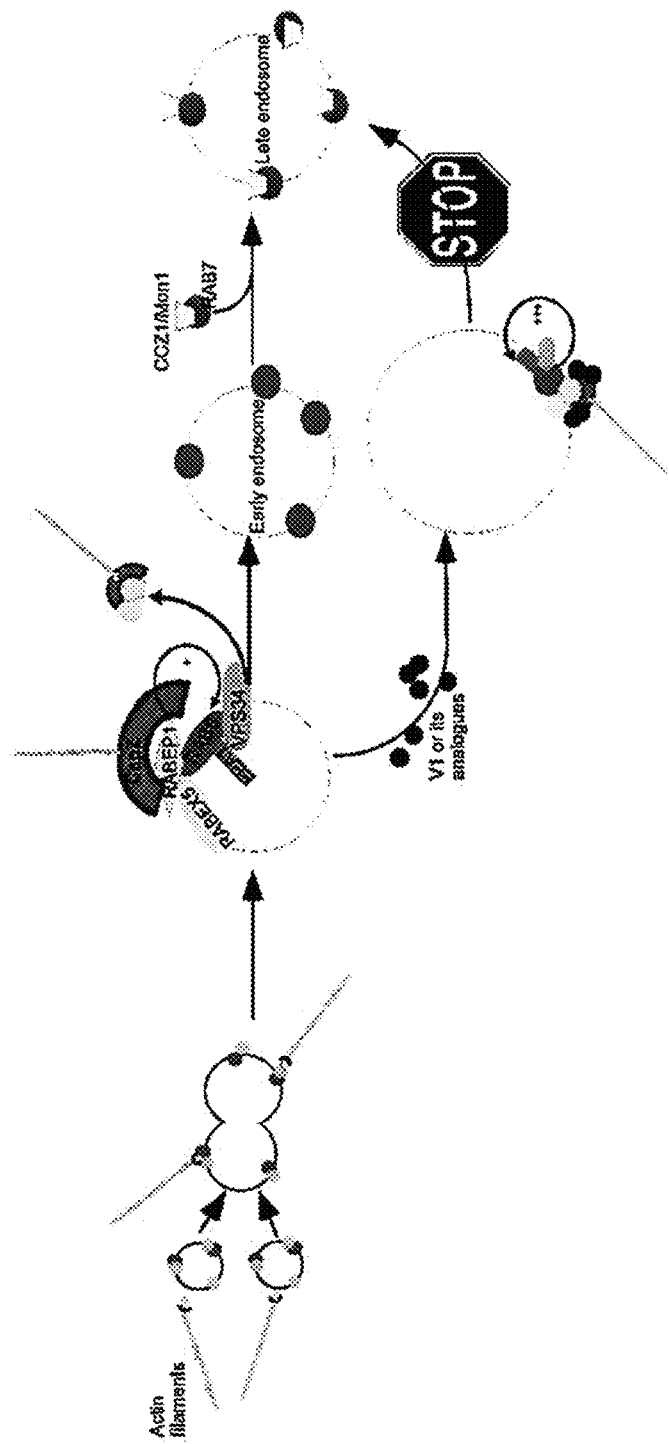
FIG. 22E is a schematic diagram illustrating the role of CapZ in endosomal trafficking and how V1 locks CapZ on the endosome to inhibit endocytosis.

The release of CapZ from matured earlier endosomes was further studied to examine whether such release is required for early endosome transition to late endosome. The studies was adopted a strategy of which RAB5 was conjugated with a rapamycin-binding motif of mTOR (FRB) whereas CapZβ was conjugated with a FK506-binding protein (FKBP), forming a rapamycin-induced protein-protein interaction system illustrated in FIG. 22A, thereby reasoning that rapamycin-triggered tethering of CapZ to endosomes should phenocopy V1 treatment to certain extent. As shown in FIG. 22B, rapamycin treatment indeed markedly enlarged the RAB5-positive endosomes, and these endosomes exhibited strong co-localization with CapZ. EGFR degradation assay was then performed in control or RAB5-FKBP and RAB5-FRB-expressing HeLa cells treated with or without rapamycin. As shown in FIG. 22C, rapamycin alone had very subtle effects on EGFR degradation in the control cells. However, EGFR degradation in RAB5-FKBP and RAB5-FRB-expressing cells was significantly delayed as compared with the control cells, and this degradation was further inhibited by rapamycin treatment (FIG. 22C). Likewise, rapamycin treatment of RAB5-FKBP and RAB5-FRB-expressing cells inhibited transferrin degradation as compared with the cells without rapamycin treatment (FIG. 22D). Taken together, these data indicate that the release of CapZ from endosomes is required for the transition of early endosomes to late endosomes, and locking CapZ on the endosome by 6-morpholino-1,3,5-triazine derivatives such as V1 would inhibit endocytosis and lead to a cascade of actions that inhibit metastasis of cancer cells (FIG. 22E).

Example 6

Figure 23A:
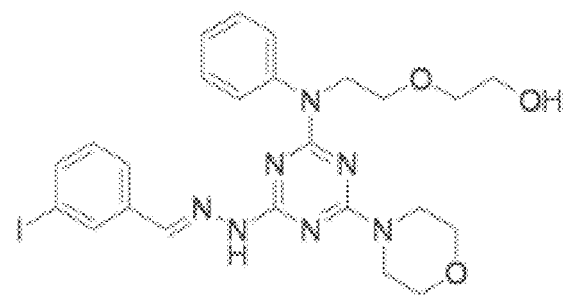
FIG. 23A is a schematic diagram illustrating the structure of 6J-1.
Figure 23B:
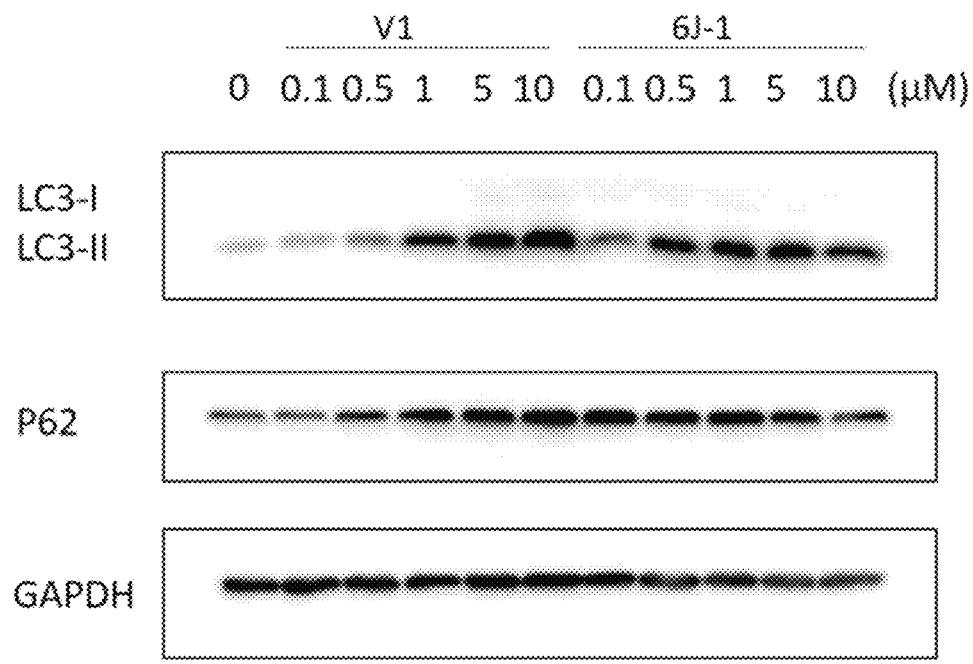
FIG. 23B is a series of immunoblots showing that 6J-1 induces comparable accumulation of LC3-II and p62 in HeLa cells as V1.
Figure 24A:
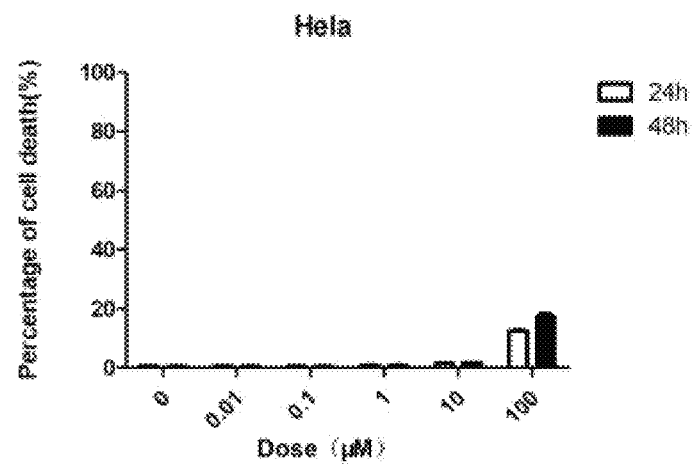
FIG. 24A is a bar chart showing the percentage of cell death of HeLa cells treated with or without 6J-1 at the indicated concentrations for 24 or 48 h.
Figure 24B:
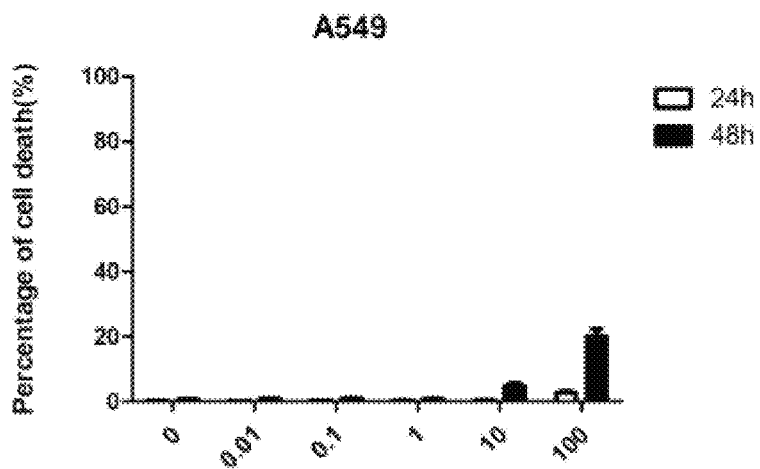
FIG. 24B is a bar chart showing the percentage of cell death of A549 cells treated with or without 6J-1 at the indicated concentrations for 24 or 48 h.
Figure 24C:
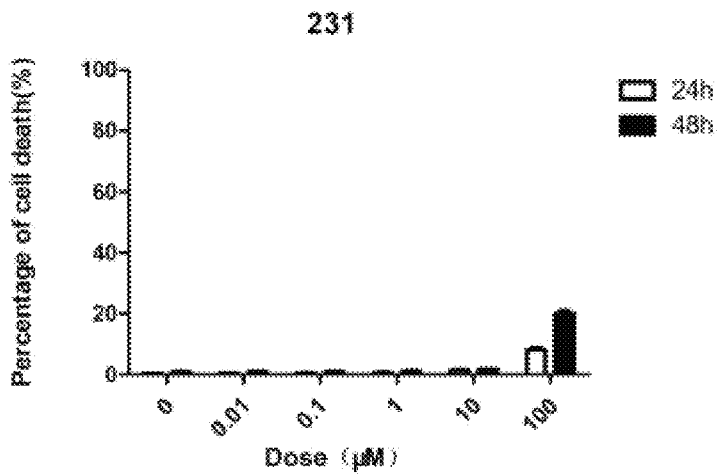
FIG. 24C is a bar chart showing the percentage of cell death of MDA-MB-231 cells treated with or without 6J-1 at the indicated concentrations for 24 or 48 h.
Figure 25A:
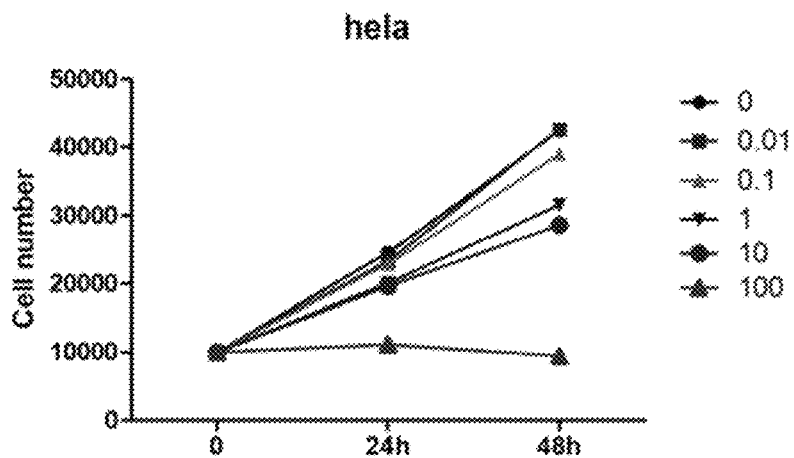
FIG. 25A is a line chart showing the number of HeLa cells treated with or without 6J-1 at the indicated concentrations for 0, 24 or 48 h.
Figure 25B:
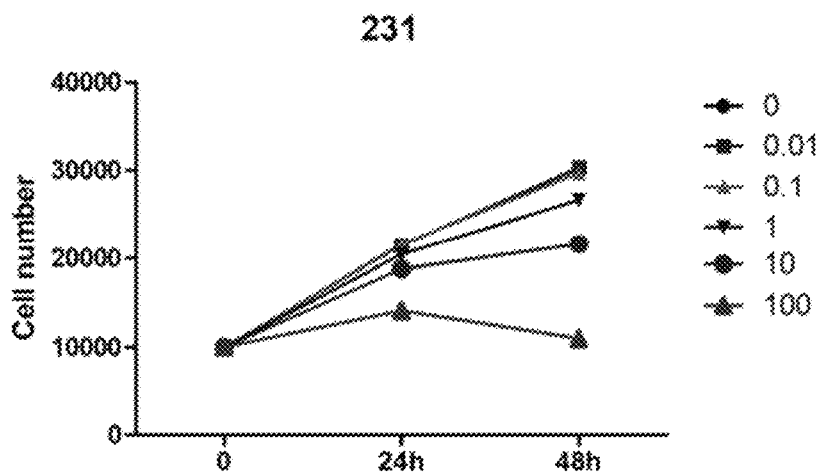
FIG. 25B is a line chart showing the number of MDA-MB-231 cells treated with or without 6J-1 at the indicated concentrations for 0, 24 or 48 h.
Figure 25C:
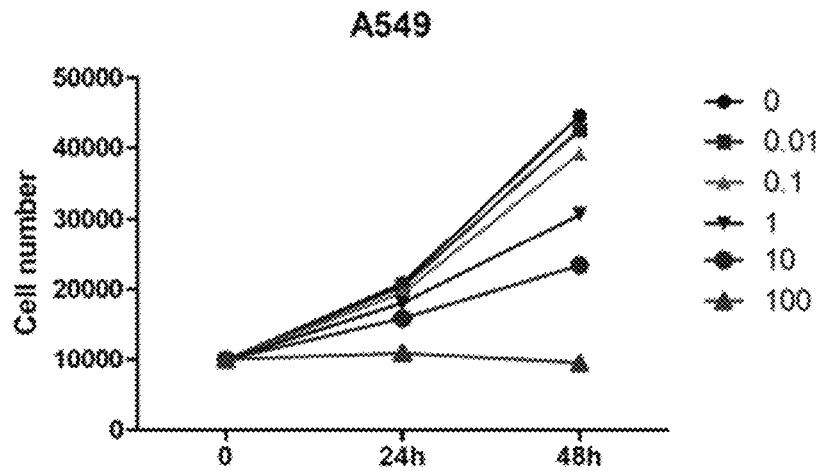
FIG. 25C is a line chart showing the number of A549 cells treated with or without 6J-1 at the indicated concentrations for 0, 24 or 48 h.

The Inhibitory Effect of 6-morpholino-1,3,5-triazine Derivatives on Endosomal Trafficking and Metastasis In this example, a 6-morpholino-1,3,5-triazine derivative, 6J-1 was synthesized and used as an exemplary example to illustrate the inhibitory effect of 6-morpholino-1,3,5-triazine derivatives on endosomal trafficking and metastasis. The structure of 6J-1 is shown in FIG. 23A. As illustrated above, the induction of accumulation of LC3-II and p62 by biotin-V1 would accompany with the induction of vacuoles as well as the inhibition of transferrin degradation (see Example 4). Herein, as shown in FIG. 23B, the results of immunoblotting of V1 showed that it is capable of inducing the accumulation of LC3-II and p62. Similarly, the 6-morpholino-1,3,5-triazine derivative, 6J-1 showed a highly comparable result as V1, suggesting that 6J-1 possesses the ability of inducing vacuoles as well as inhibiting transferrin degradation, which are crucial features for inhibiting endosomal trafficking.

The cytotoxicity of 6J-1 on different cancer cell lines has been examined by PI staining, and the cell number of living cells was quantified as well. As shown in FIGS. 24A-24C and 25A-25C, 6J-1 is non-cytotoxic to HeLa, A549, or MDA-MB-231 cells at concentrations of 0.01-10 μM. Even at a concentration of as high as 100 μM, there were over 80% of the 6J-1-treated cells remained alive. All these data suggest that 6J-1 exhibited a very low cytotoxicity.

Figure 26:
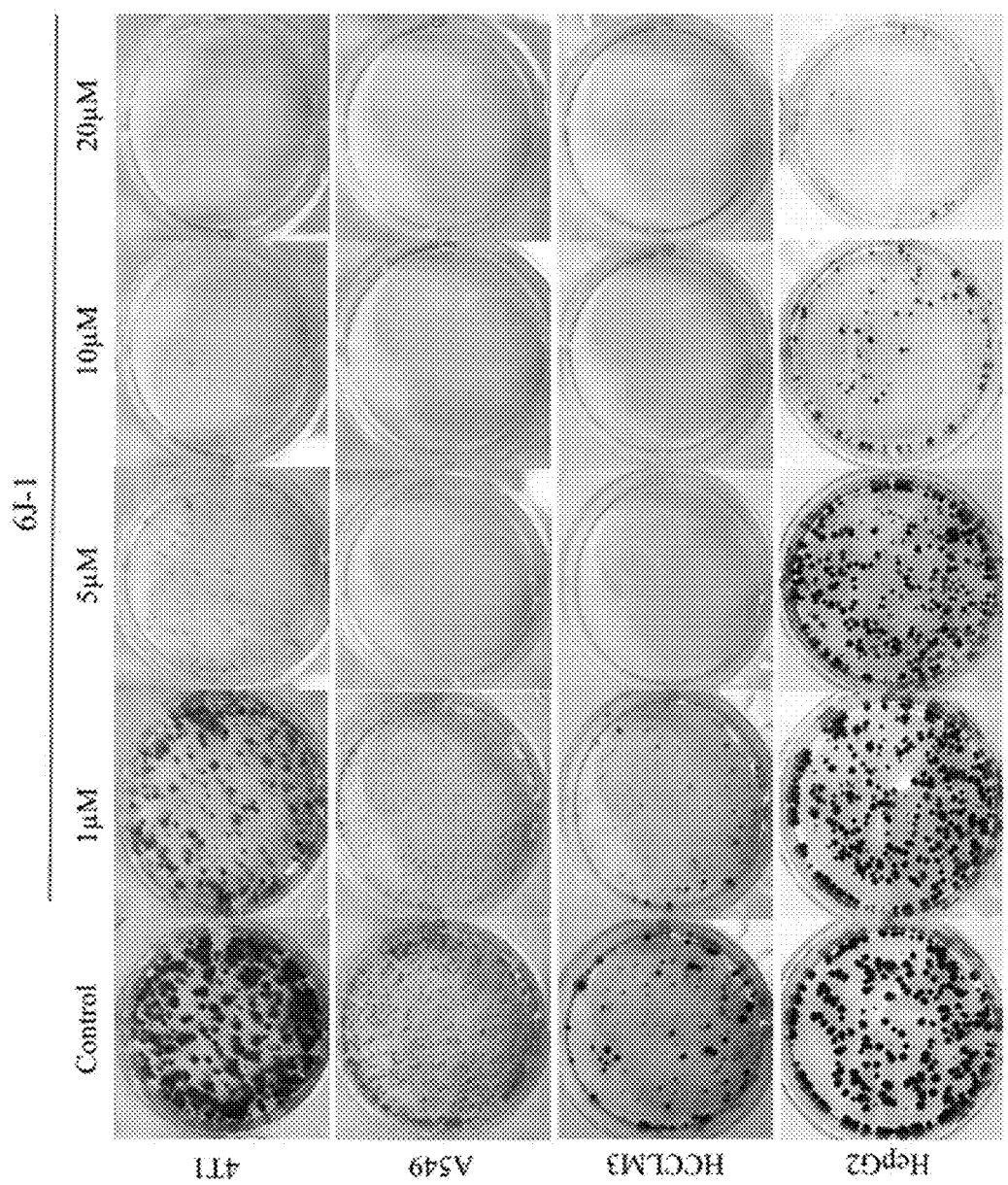
FIG. 26 is a series of optical images showing colony formation of 4T1, A549, HCCLM3, and HepG2 cells treated with or without 6J-1 at the indicated concentrations.
Figure 27A:
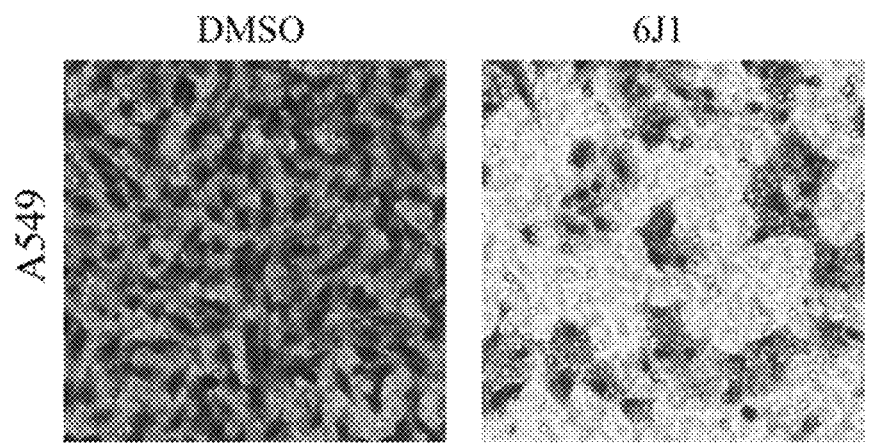
FIG. 27A is a pair of microscopic images showing the migration of A549 cells treated with or without 6J-1 (1 μM).
Figure 27B:
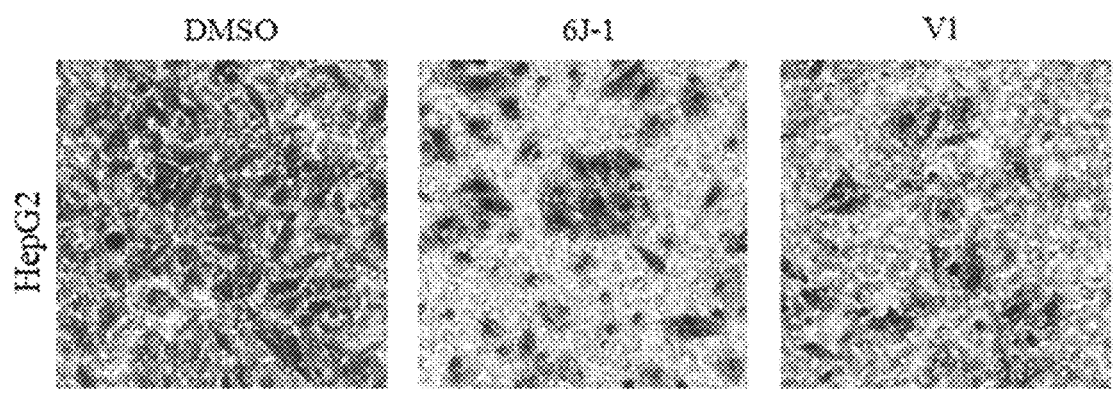
FIG. 27B is a series of microscopic images showing the migration of HepG2 cells treated with or without V1 (1 μM) or 6J-1 (1 μM).
Figure 28:
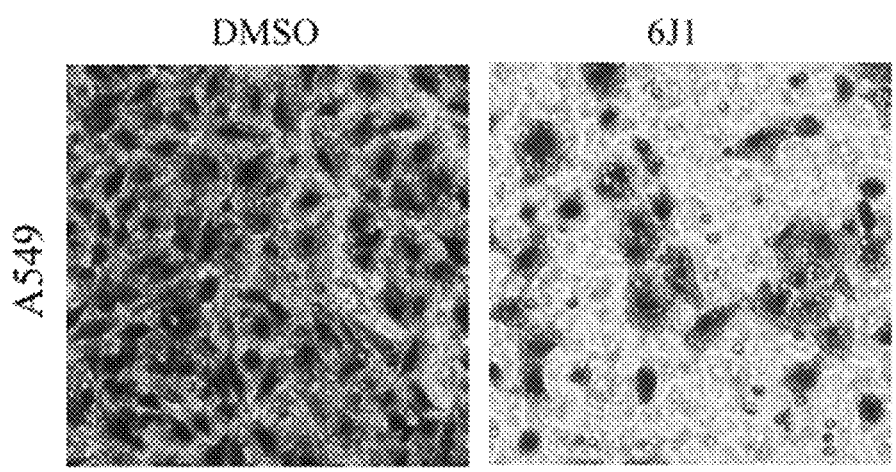
FIG. 28 is a pair of microscopic images showing the invasion of A549 cells treated with or without 6J-1 (1 μM).

The inhibitory effect of 6J-1 on colony formation of several cancer cell lines, including 4T1, A549, HCCLM3, and HepG2 has been examined. As shown in FIG. 26, 6J-1 exhibited an inhibitory on the colony formation of all the aforementioned cell lines in a dose dependent manner. Apart from inhibiting cancer cell colony formation, 6J-1 is capable of inhibiting migration and invasion of cancer cells as well (FIGS. 27A and 27B, 28). Overall, 6J-1 is found to be as potent as V1.

Figure 29A:
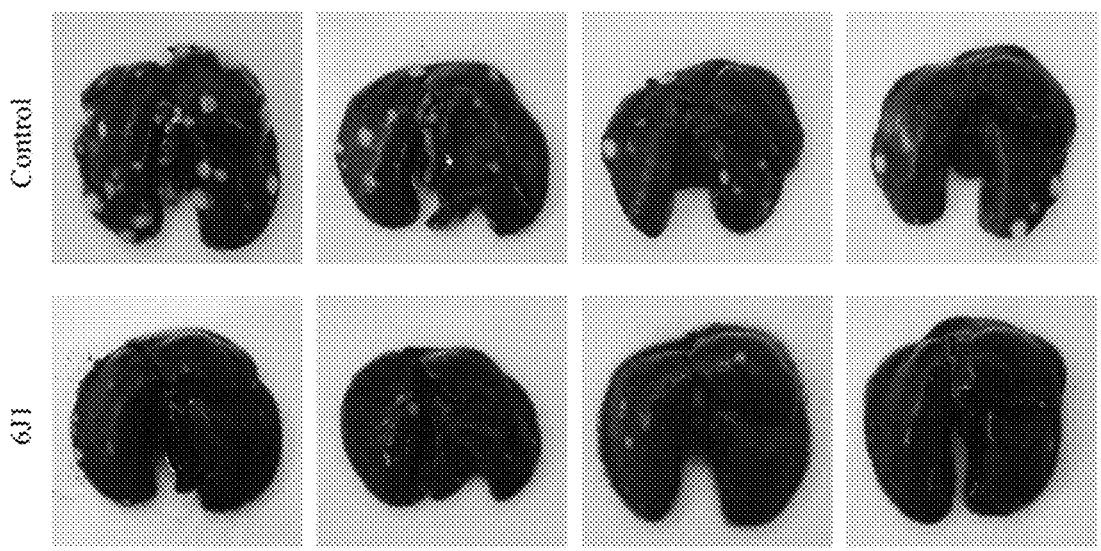
FIG. 29A is a series of optical images showing the excised lungs of female nude mice treated with a buffer or 6J-1 (30 mg/kg, oral delivery, daily) for 4 weeks.
Figure 29B:
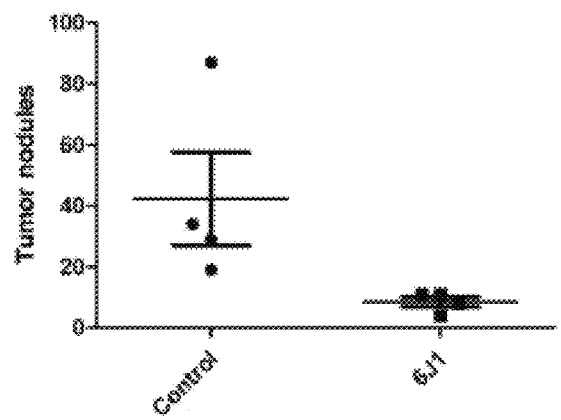
FIG. 29B is a line plot showing the number of tumor nodules in the excised lungs of the mice of FIG. 29A.
Figure 29C:
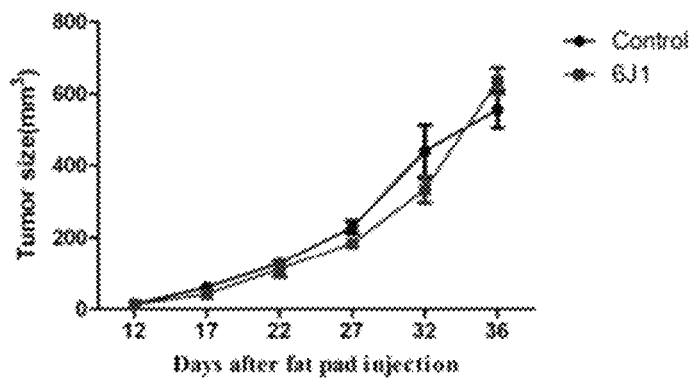
FIG. 29C is a line chart showing the tumor size in fat pat of the female nude mice of FIG. 29A against days after treatment.
Figure 29D:
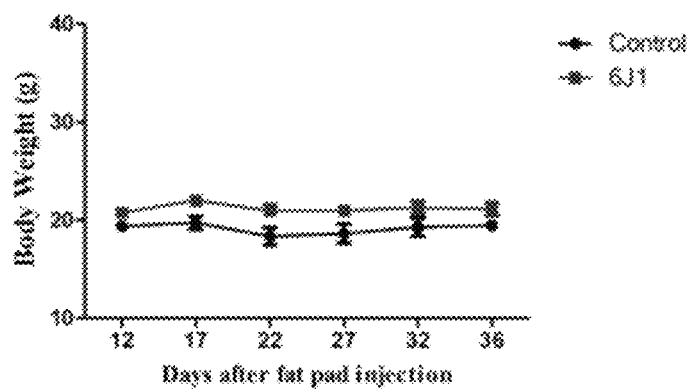
FIG. 29D is a line chart showing the body weight of the mice of FIG. 29A against days of treatment.

Lastly, 6J-1 was administered to a spontaneous cancer mouse model by fat pad injecting 4T1 mouse breast cancer cells into nude mice to determine its anti-metastatic effect in vivo. After tumors were palpable (~5 mm, around day 9), the mice were randomly divided into three groups (four mice per group) orally treated with or without 6J-1 (30 mg/kg) every day. After 4 weeks, the mice were sacrificed; the primary tumors and lungs of the mice were harvested for analysis. Importantly, 6J-1 significantly inhibited the metastasis of 4T1 cells in the nude mice, manifested by fewer tumor nodules in the lungs of 6J-11-treated groups compared with the control groups (FIGS. 29A and 29B). Notably, V1 did not affect the growth of primary tumor (FIG. 29C), or the mouse weight (FIG. 29D).

The invention claimed is:

1. A method of treating metastatic cancer in a subject, wherein the metastatic cancer is selected from the group consisting of breast cancer, lung cancer, and a combination thereof, comprising administering an effective amount of a capping protein Z stabilizer to the subject, wherein the capping protein Z stabilizer inhibits endosomal trafficking and comprises the following structure:

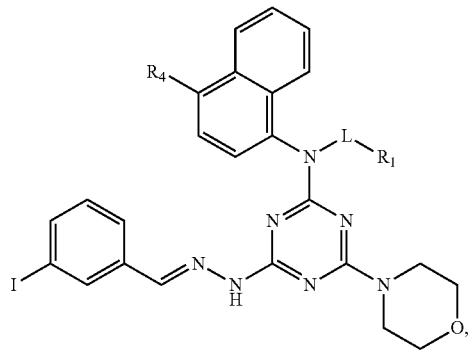

wherein:

$R_1$ is a hydrogen atom, a methyl group, a cyano group, an ethynyl group, an ethoxycarbonyl group, or a phenyl group;

$R_4$ is a hydrogen atom, a chloro or a fluoro group; and

L is a linker group of —$(CH_2)_m$— or —$(CH_2CH_2O)_{m'}$— with m being 3, 4 or 5, and m' being 2.

2. A method of treating metastatic cancer in a subject comprising administering an effective amount of a capping protein Z stabilizer to the subject, wherein the metastatic cancer is selected from the group consisting of breast cancer, lung cancer, and a combination thereof, wherein the capping protein Z stabilizer inhibits endosomal trafficking and comprises a structure of Formula (II):

Formula (II)

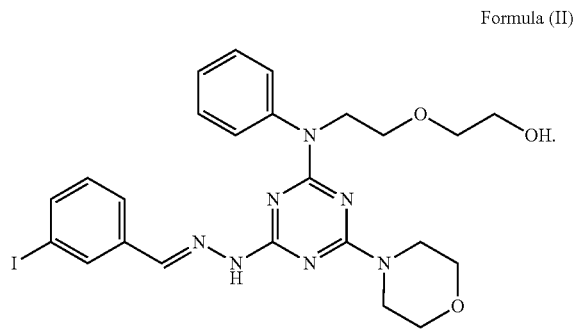 [SMILES: OCCOCCN(c1ccccc1)c1nc(N/N=C/c2cccc(I)c2)nc(N2CCOCC2)n1]

3. The method of claim 1, wherein the capping protein Z stabilizer is administered to the subject by a route selected from the group consisting of oral delivery, intravenous delivery, intradermal delivery, intraperitoneal delivery and intramuscular delivery.

4. The method of claim 1, wherein the capping protein Z stabilizer is administered in combination with one or more chemotherapy drug to the subject.

5. The method of claim 4, wherein the chemotherapy drug is selected from doxorubicin, taxol, 5-Fu, or temirolimus.

6. A method of inhibiting metastasis of cancer cells, wherein the cancer cells are selected from the group consisting of breast cancer, lung cancer, and a combination thereof, comprising administering to the cancer cells an effective amount of a capping protein Z stabilizer, wherein the capping protein Z stabilizer inhibits endosomal trafficking and comprises the following structure:

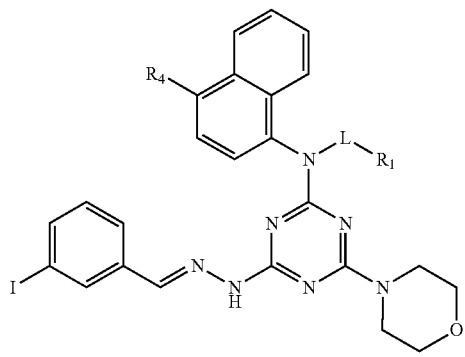

wherein:
R₁ is a hydrogen atom, a methyl group, a cyano group, an ethynyl group, an ethoxycarbonyl group, or a phenyl group;
R₄ is hydrogen atom, a chloro or a fluoro group; and
L is a linker group of —(CH₂)$_m$— or —(CH₂CH₂O)$_{m'}$— with m being 3, 4 or 5, and m' being 2.

7. A method of inhibiting metastasis of cancer cells, wherein the cancer cells are selected from the group consisting of breast cancer, lung cancer, and a combination thereof, comprising administering to the cancer cells an effective amount of a capping protein Z stabilizer, wherein the capping protein Z stabilizer inhibits endosomal trafficking and comprises, a structure of Formula (II):

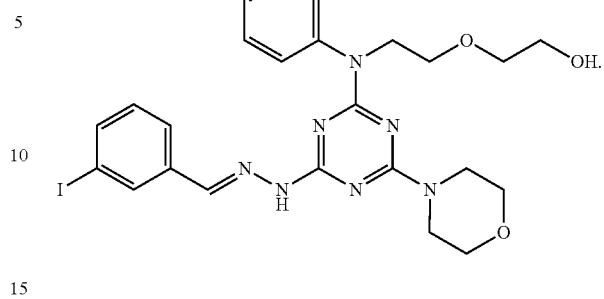

Formula (II)

8. The method of claim 6, wherein the capping protein Z stabilizer is administered to the cancer cells in combination with one or more chemotherapy drug.

9. The method of claim 8, wherein the chemotherapy drug is selected from doxorubicin, taxol, 5-Fu, or temirolimus.

10. The method of claim 7, wherein the capping protein Z stabilizer is administered to the cancer cells in combination with one or more chemotherapy drugs.

11. The method of claim 10, wherein the chemotherapy drug is selected from doxorubicin, taxol, 5-Fu, or temirolimus.

* * * * *